US008518890B2

(12) United States Patent
Hara et al.

(10) Patent No.: US 8,518,890 B2
(45) Date of Patent: Aug. 27, 2013

(54) REMEDIES FOR SEX HORMONE DEPENDENT DISEASE

(75) Inventors: Takahito Hara, Osaka (JP); Masami Kusaka, Kobe (JP)

(73) Assignee: Takeda Pharmaceutical Company Limited, Osaka (JP)

(*) Notice: Subject to any disclaimer, the term of this patent is extended or adjusted under 35 U.S.C. 154(b) by 842 days.

(21) Appl. No.: 11/864,022

(22) Filed: Sep. 28, 2007

(65) Prior Publication Data

US 2008/0138426 A1 Jun. 12, 2008

Related U.S. Application Data

(63) Continuation of application No. 10/507,044, filed as application No. PCT/JP03/02783 on Mar. 10, 2003, now abandoned.

(30) Foreign Application Priority Data

Mar. 11, 2002 (JP) .................................. 2002-65734

(51) Int. Cl.
*A61K 38/00* (2006.01)
*A61K 38/24* (2006.01)
*A61P 35/00* (2006.01)
*A61P 5/06* (2006.01)
*C07K 14/59* (2006.01)

(52) U.S. Cl.
USPC .......................... 514/19.5; 514/10.1; 514/10.2

(58) Field of Classification Search
None
See application file for complete search history.

(56) References Cited

U.S. PATENT DOCUMENTS

| | | | |
|---|---|---|---|
| 4,071,622 A | 1/1978 | Johnson et al. | |
| 4,472,382 A | 9/1984 | Labrie et al. | |
| 5,110,904 A | 5/1992 | Haviv et al. | |
| 5,550,107 A | 8/1996 | Labrie | |
| 5,677,184 A | 10/1997 | Onda et al. | |
| 5,981,550 A | 11/1999 | Goulet et al. | |
| 6,077,847 A | 6/2000 | Walsh et al. | |
| 6,113,943 A | 9/2000 | Okada et al. | |
| 2008/0138426 A1* | 6/2008 | Hara et al. | 424/490 |

FOREIGN PATENT DOCUMENTS

| | | |
|---|---|---|
| EP | 0413209 A1 | 2/1991 |
| EP | 1 136 079 A1 | 9/2001 |
| JP | 3-101695 A | 4/1991 |
| JP | 4-504848 A | 8/1992 |
| JP | 11-507050 A | 6/1999 |
| WO | WO 90/10462 | 9/1990 |
| WO | WO 96/37201 A2 | 11/1996 |
| WO | WO 96/40150 | 12/1996 |
| WO | WO 98/24451 A1 | 6/1998 |
| WO | WO 00/40259 A1 | 7/2000 |
| WO | WO 00/57892 | 10/2000 |

OTHER PUBLICATIONS

Sharifi et al. Therapeutic effects of leuprorelin micorspheres in prostate cancer. Advanced Drug Delivery Reviews. 1997. 20, pp. 121-128.*
Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
Prostate cancer, advance or metastatic. Blu of California. https://www.blueshieldca.com/hw/articles/hw_article.jsp?articleld=HWUH1681&fromTopics=all_topics&_requestid=398582#uh1690, accessed Feb. 25, 2008. 17 pages.*
Office Action dated Apr. 8, 2009, in corresponding JP Application 2003-062996, 6 pages, with English translation, 10 pages.
Supplementary European Search Report dated Jun. 10, 2009, in corresponding EP 03744036.9, 6 pages.
Gibbs et al., "Androgen Deprivation and Antagonism in the Treatment of Advanced Prostatic Carcinoma," Clinical Oncology, Jan. 1, 1996, 8(6):346-352.
Communication dated Jul. 14, 2011, in corresponding EP 03 744 036.9, 4 pages.
Dawson et al., "A Pilot Trial of Chemohormonal Therapy for Metastatic Prostate Carcinoma," Cancer, Jan. 1, 1992, 69(1):213-218.
Office Action dated Nov. 6, 2009, in corresponding Canadian Patent Application No. 2,478,827, 4 pages.
Office Action dated Nov. 5, 2009, in corresponding European Patent Application No. 03 744 036.9, 9 pages.
El-Rayes et al., "Hormonal therapy for prostate cancer: past, present and future," Expert Rev. Anticancer Ther., 2002, 2(1):37-47.
Leibowitz et al., "Treatment of Localized Prostate Cancer with Intermittent Triple Androgen Blockade: Preliminary Results in 110 Consecutive Patients," The Oncologist, 2001, 6:177-182.
Neymark et al., "Cost-effectiveness of the addition of early hormonal therapy in locally advanced prostate cancer: results decisively determined by the cut-off time-point chosen for the analysis," European Journal of Cancer, 2001, 37:1768-1774.
Persad, R., "Leuprorelin acetate in prostate cancer: A European update," Journal fur Urologie and Urogynakologie, 2002, 9(Sonderheft 3) (Ausgabe für Österreich):16-26.
Smith et al., "Inhibitors of steroidogenesis as agents for the treatment of hormone-dependent cancers," Exp. Opin. Ther. Patents, 2001, 11(5):789-824.
Stricker, Hans J., "Luteinizing hormone-releasing hormone antagonists in prostate cancer," Urology, 2001, 58(Suppl. 2A):24-27.
Kokontis et al., "Increased Androgen Receptor Activity and Altered c-myc Expression in Prostate Cancer Cells after Long-Term Androgen Deprivation," Cancer Research, 1994, pp. 1566-1573, vol. 54.
Umekita et al., "Human Prostate Tumor Growth in Athymic Mice: Inhibition by Androgens and Stimulation by Fiasteride," Proc. Natl. Acad. Sci. USA, 1996, pp. 11802-11807, vol. 93.

* cited by examiner

Primary Examiner — Marcela M Cordero Garcia
(74) Attorney, Agent, or Firm — Foley & Lardner LLP

(57) ABSTRACT

A combination agent containing an LHRH receptor agonist or antagonist and an androgen receptor agonist, which is useful as an agent for the prophylaxis or treatment of hormone-dependent diseases and the like, is provided.

6 Claims, 1 Drawing Sheet

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (2)..(2)
<223> OTHER INFORMATION: His, Tyr, Trp or p-NH2-Phe
<220> FEATURE:
<221> NAME/KEY: MOD_RES
<222> LOCATION: (5)..(5)
```

```
<223> OTHER INFORMATION: Tyr or Phe
<220> FEATURE:
<221> NAME/KEY: MOD_RES
<222> LOCATION: (6)..(6)
<223> OTHER INFORMATION: Gly or D type amino acid residue
<220> FEATURE:
<221> NAME/KEY: MOD_RES
<222> LOCATION: (7)..(7)
<223> OTHER INFORMATION: Leu, Ile or Norleucine
<220> FEATURE:
<223> OTHER INFORMATION: see specification as filed for detailed
      description of substitutions and preferred embodiments

<400> SEQUENCE: 1

Glu Xaa Trp Ser Xaa Xaa Xaa Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (10)..(10)
<223> OTHER INFORMATION: Gly-NH2

<400> SEQUENCE: 2

Pro His Trp Ser Tyr Gly Leu Arg Pro Gly
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: O-tert-butyl-D-Ser
<220> FEATURE:
<221> NAME/KEY: MOD_RES
<222> LOCATION: (9)..(9)
<223> OTHER INFORMATION: Pro-NH-CH2-CH3

<400> SEQUENCE: 3

Pro His Trp Ser Tyr Ser Leu Arg Pro
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
```

```
<222> LOCATION: (10)..(10)
<223> OTHER INFORMATION: Gly-NH2

<400> SEQUENCE: 4

Pro His Trp Ser Tyr Trp Leu Arg Pro Gly
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: O-tert-butyl-D-Ser
<220> FEATURE:
<221> NAME/KEY: MOD_RES
<222> LOCATION: (9)..(9)
<223> OTHER INFORMATION: Pro-NH-NH-CO-NH2

<400> SEQUENCE: 5

Pro His Trp Ser Tyr Ser Leu Arg Pro
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: D-3-(2-naphthyl)alanine
<220> FEATURE:
<221> NAME/KEY: MOD_RES
<222> LOCATION: (10)..(10)
<223> OTHER INFORMATION: Gly-NH2

<400> SEQUENCE: 6

Pro His Trp Ser Tyr Xaa Leu Arg Pro Gly
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: Nim-benzyl-D-His
<220> FEATURE:
<221> NAME/KEY: MOD_RES
<222> LOCATION: (9)..(9)
<223> OTHER INFORMATION: Pro-NH-CH2-CH3
```

```
<400> SEQUENCE: 7

Pro His Trp Ser Tyr His Leu Arg Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (9)..(9)
<223> OTHER INFORMATION: Pro-NH-CH2-CH2-NH2

<400> SEQUENCE: 8

Pro His Trp Ser Tyr Trp Leu Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: 2-Methyl-Trp
<220> FEATURE:
<221> NAME/KEY: MOD_RES
<222> LOCATION: (9)..(9)
<223> OTHER INFORMATION: Pro-NH-CH2-CH3

<400> SEQUENCE: 9

Pro His Trp Ser Tyr Trp Leu Arg Pro
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: MOD_RES
<222> LOCATION: (6)..(6)
<223> OTHER INFORMATION: D-3-Methyl-Val
<220> FEATURE:
<221> NAME/KEY: MOD_RES
<222> LOCATION: (9)..(9)
<223> OTHER INFORMATION: Pro-NH-C2H5

<400> SEQUENCE: 10

Pro His Trp Ser Tyr Val Leu Arg Pro
1               5
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: C4OCONHCH2CO-D-3-(2-naphthyl)alanine
<220> FEATURE:
<221> NAME/KEY: MOD_RES
<222> LOCATION: (2)..(2)
<223> OTHER INFORMATION: D4ClPhe
<220> FEATURE:
<221> NAME/KEY: MOD_RES
<222> LOCATION: (3)..(3)
<223> OTHER INFORMATION: D3Pal
<220> FEATURE:
<221> NAME/KEY: MOD_RES
<222> LOCATION: (5)..(5)
<223> OTHER INFORMATION: N-Methyl-Tyr
<220> FEATURE:
<221> NAME/KEY: MOD_RES
<222> LOCATION: (6)..(6)
<223> OTHER INFORMATION: DLys(Nic)
<220> FEATURE:
<221> NAME/KEY: MOD_RES
<222> LOCATION: (8)..(8)
<223> OTHER INFORMATION: Lys(Nisp)
<220> FEATURE:
<221> NAME/KEY: MOD_RES
<222> LOCATION: (10)..(10)
<223> OTHER INFORMATION: D-Ala-NH2
<220> FEATURE:
<223> OTHER INFORMATION: see specification as filed for detailed
      description of preferred embodiments

<400> SEQUENCE: 11

Xaa Phe Xaa Ser Tyr Lys Leu Lys Pro Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: C4OCONHCH2CO-D-3-(2-naphthyl)alanine
<220> FEATURE:
<221> NAME/KEY: MOD_RES
<222> LOCATION: (2)..(2)
<223> OTHER INFORMATION: D4ClPhe
<220> FEATURE:
<221> NAME/KEY: MOD_RES
<222> LOCATION: (3)..(3)
<223> OTHER INFORMATION: D3Pal
<220> FEATURE:
<221> NAME/KEY: MOD_RES
<222> LOCATION: (5)..(5)
<223> OTHER INFORMATION: N-Methyl-Tyr
<220> FEATURE:
<221> NAME/KEY: MOD_RES
<222> LOCATION: (6)..(6)
<223> OTHER INFORMATION: DLys(Nic)
<220> FEATURE:
<221> NAME/KEY: MOD_RES
<222> LOCATION: (8)..(8)
<223> OTHER INFORMATION: Lys(Nisp)
<220> FEATURE:
<221> NAME/KEY: MOD_RES
<222> LOCATION: (10)..(10)
```

-continued

```
<223> OTHER INFORMATION: D-Ala-NH2-CH3COOH, D-Ala-NH2-(CH3COOH)2 or
      D-Ala-NH2-(CH3COOH)3
<220> FEATURE:
<223> OTHER INFORMATION: see specification as filed for detailed
      description of preferred embodiments

<400> SEQUENCE: 12

Xaa Phe Xaa Ser Tyr Lys Leu Lys Pro Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-Acetyl-D-3-(2-naphthyl)alanine
<220> FEATURE:
<221> NAME/KEY: MOD_RES
<222> LOCATION: (2)..(2)
<223> OTHER INFORMATION: D4ClPhe
<220> FEATURE:
<221> NAME/KEY: MOD_RES
<222> LOCATION: (3)..(3)
<223> OTHER INFORMATION: D3Pal
<220> FEATURE:
<221> NAME/KEY: MOD_RES
<222> LOCATION: (6)..(6)
<223> OTHER INFORMATION: DhArg(Et2)
<220> FEATURE:
<221> NAME/KEY: MOD_RES
<222> LOCATION: (8)..(8)
<223> OTHER INFORMATION: hArg(Et2)
<220> FEATURE:
<221> NAME/KEY: MOD_RES
<222> LOCATION: (10)..(10)
<223> OTHER INFORMATION: D-Ala-NH2

<400> SEQUENCE: 13

Xaa Phe Xaa Ser Tyr Arg Leu Arg Pro Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-Acetyl-D-3-(2-naphthyl)alanine
<220> FEATURE:
<221> NAME/KEY: MOD_RES
<222> LOCATION: (2)..(2)
<223> OTHER INFORMATION: D4ClPhe
<220> FEATURE:
<221> NAME/KEY: MOD_RES
<222> LOCATION: (3)..(3)
<223> OTHER INFORMATION: D3Pal
<220> FEATURE:
<221> NAME/KEY: MOD_RES
<222> LOCATION: (6)..(6)
<223> OTHER INFORMATION: DhArg(Et2)
<220> FEATURE:
<221> NAME/KEY: MOD_RES
<222> LOCATION: (8)..(8)
<223> OTHER INFORMATION: hArg(Et2)
<220> FEATURE:
<221> NAME/KEY: MOD_RES
<222> LOCATION: (10)..(10)
```

```
<223> OTHER INFORMATION: D-Ala-NH2-CH3COOH, D-Ala-NH2-(CH3COOH)2 or
      D-Ala-NH2-(CH3COOH)3

<400> SEQUENCE: 14

Xaa Phe Xaa Ser Tyr Arg Leu Arg Pro Ala
1               5                   10
```

REMEDIES FOR SEX HORMONE DEPENDENT DISEASE

TECHNICAL FIELD

The present invention relates to a novel pharmaceutical agent comprising an LHRH (luteinizing hormone-releasing hormone) receptor agonist or antagonist or a salt thereof in combination with an androgen receptor agonist or a salt thereof, an agent for the prophylaxis or treatment of prostate cancer, which comprises a non-steroidal androgen receptor agonist or a salt thereof and a method for treating prostate cancer and the like.

BACKGROUND ART

Gonadotropin releasing hormone (GnRH, also referred to as LHRH) is a decapeptide consisting of 10 amino acids, which is produced in the hypothalamus and known to control secretion of luteinizing hormone (LH), follicle stimulating hormone (FSH) and the like through receptors considered to be present in the anterior pituitary, based on which GnRH shows a variety of physiological activities such as ovulation induction and the like. Therefore, specific and selective antagonists or agonists to these receptors control hormone action of GnRH produced from the hypothalamus, and control secretion of anterior pituitary hormone such as LH, FSH and the like. Therefore, secretion of estrogen in females and of testosterone in males is suppressed and a prophylactic or therapeutic effect on sex hormone-dependent diseases can be expected.

For example, leuprorelin acetate, which is an agonist of gonadotropin releasing hormone receptor, has 20 to 100 times the activity of natural GnRH, and is a compound that is not easily metabolized. Repetitive administration thereof causes down regulation of GnRH receptors and decreases release and production of gonadotrophic hormone in the pituitary gland, which is demonstrated by, for example, reduced reactivity to gonadotrophic hormone and lowered productivity of testosterone to a sterilization level in the testes, and lowered productivity of estrogen in the ovaries. As a result, it can be a useful prophylactic or therapeutic agent for these hormone-dependent diseases, such as prostate cancer, prostatic hypertrophy, masculinism, hypertrichiasis, male-pattern baldness, male infantile precocity, female infantile precocity, precocious puberty, breast cancer, uterine cancer, mastopathy, hysteromyoma, endometriosis and the like. In fact, leuprorelin acetate has been used widely in clinical situations as a therapeutic drug for prostate cancer, breast cancer, endometriosis, hysteromyoma, precocious puberty and the like.

However, certain kinds of cancers acquire an ability to grow even at an extremely low concentration of hormone (e.g., androgen at sterilization level). The present invention aims at provision of a pharmaceutical agent and a prophylactic or therapeutic method based on an LHRH agonist or antagonist or a silt thereof that improves a prophylactic or therapeutic effect on various hormone-dependent diseases.

DISCLOSURE OF THE INVENTION

The present inventors have conducted intensive studies in an attempt to solve the aforementioned problems and found that a combined use of an LHRH receptor agonist or antagonist or a salt thereof with an androgen receptor agonist or a salt thereof, which are exacerbating factors of hormone-dependent diseases, unexpectedly strikingly enhances a prophylactic or therapeutic effect on various diseases by an LHRH agonist or antagonist or a salt thereof, and reduces side effects. Based on these findings, the present inventors have further studied, which resulted in the completion of the present invention.

Accordingly, the present invention relates to (1) a pharmaceutical agent comprising 1) an LHRH receptor agonist or antagonist or a salt thereof in combination with 2) an androgen receptor agonist or a salt thereof;

(2) the pharmaceutical agent of the aforementioned (1), wherein the LHRH receptor agonist is leuprorelin;

(3) the pharmaceutical agent of the aforementioned (1), wherein the androgen receptor agonist is a steroidal androgen receptor agonist;

(4) the pharmaceutical agent of the aforementioned (3), wherein the steroidal androgen receptor agonist is one or more compounds selected from the group consisting of dehydroepiandrosterone, testosterone, dihydrotestosterone, androstenedione, Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylestrenol and Norbolethone, or a salt thereof;

(5) the pharmaceutical agent of the aforementioned (1), wherein the androgen receptor agonist is a non-steroidal androgen receptor agonist;

(6) the pharmaceutical agent of the aforementioned (1), which is an agent for the prophylaxis or treatment of a hormone-dependent disease;

(7) the pharmaceutical agent of the aforementioned (6), wherein the hormone-dependent disease is prostate cancer;

(8) the pharmaceutical agent of the aforementioned (1), wherein the LHRH receptor agonist or antagonist or a salt thereof is used as a sustained-release preparation or an embedded agent;

(9) the pharmaceutical agent of the aforementioned (8) wherein the sustained-release preparation is a sustained-release microcapsule;

(10) the pharmaceutical agent of the aforementioned (9), wherein the sustained-release microcapsule is a long-term sustained-release microcapsule that releases an LHRH receptor agonist or antagonist or a salt thereof for not less than 2 months;

(11) an agent for the prophylaxis or treatment of bone metastatic prostate cancer, which comprises an androgen receptor agonist or a salt thereof;

(12) the agent of the aforementioned (11), wherein the bone metastatic prostate cancer cell is highly sensitive to androgen;

(13) the agent of the aforementioned (11), wherein the androgen receptor agonist is a steroidal androgen receptor agonist;

(14) the agent of the aforementioned (13), wherein the steroidal androgen receptor agonist is one or more compounds selected from the group consisting of dehydroepiandrosterone, testosterone, dihydrotestosterone, androstenedione, Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylestrenol and Norbolethone, or a salt thereof;

(15) the agent of the aforementioned (11), wherein the androgen receptor agonist is a non-steroidal androgen receptor agonist;

(16) an agent for the prophylaxis or treatment of prostate cancer, which comprises a non-steroidal androgen receptor agonist or a salt thereof;

(17) the agent of the aforementioned (16), wherein the prostate cancer cell is highly sensitive to androgen;

(18) a method for treating prostate cancer, which comprises administering an effective amount of an LHRH receptor agonist or antagonist or a salt thereof to a mammal, and after prostate cancer cell has become highly sensitive to androgen, administering an effective amount of an androgen receptor agonist or a salt thereof;

(19) a method for treating breast cancer or uterine cancer, which comprises administering an effective amount of an LHRH receptor agonist or antagonist or a salt thereof to a mammal, and after breast cancer or uterine cancer cell has become highly sensitive to estrogen, administering an effective amount of an estrogen receptor agonist or a salt thereof;

(20) a method for treating prostate cancer, which comprises administering an effective amount of an LHRH receptor agonist or antagonist or a salt thereof in combination with an effective amount of an androgen receptor agonist or a salt thereof to a mammal;

(21) a method for treating breast cancer or uterine cancer, which comprises administering an effective amount of an LHRH receptor agonist or antagonist or a salt thereof in combination with an effective amount of an estrogen receptor agonist or a salt thereof to a mammal;

(22) a method for treating prostate cancer, which comprises administering an effective amount of an LHRH receptor agonist or antagonist or a salt thereof in combination with an effective amount of an androgen receptor agonist or a salt thereof to a mammal to shrink a prostate tumor, and then performing a surgery or radiation treatment;

(23) a method for treating breast cancer or uterine cancer, which comprises administering an effective amount of an LHRH receptor agonist or antagonist or a salt thereof in combination with an effective amount of an estrogen receptor agonist or a salt thereof to a mammal to shrink breast tumor or uterine tumor, and then performing a surgery or radiation treatment;

(24) a method for treating prostate cancer, which comprises 1) administering an androgen receptor agonist or a salt thereof to a highly androgen sensitive prostate cancer cell for a certain time period, 2) thereafter when the androgen sensitivity of the cancer cell has become lower, administering an effective amount of one or two compounds selected from an LHRH receptor agonist or antagonist and an antiandrogen drug, or a salt thereof, or when the androgen sensitivity of the cancer cell has increased, administering an effective amount of an androgen receptor agonist or a salt thereof, and 3) repeating the step 2) as necessary until an object of cancer treatment is achieved;

(25) the method of the aforementioned (24), which comprises alternately administering an effective amount of 1) an androgen receptor agonist or a salt thereof and 2) 1 or 2 compounds selected from an LHRH receptor agonist or antagonist and an antiandrogen drug, or a salt thereof;

(26) the method of the aforementioned (25), comprising changing the administration drug after a lapse of 3 months to 5 years;

(27) a method for treating breast cancer or uterine cancer, which comprises 1) administering an estrogen receptor agonist or a salt thereof to a highly estrogen sensitive breast cancer or uterine cancer cell for a certain time period, 2) thereafter when the estrogen sensitivity of the cancer cell has become lower, administering an effective amount of 1 or 2 compounds selected from an LHRH receptor agonist or antagonist and an antiestrogen drug, or a salt thereof, or when the estrogen sensitivity of the cancer cell has increased, administering an effective amount of an estrogen receptor agonist or a salt thereof, and 3) repeating the step 2) as necessary until an object of cancer treatment is achieved;

(28) the method of the aforementioned (27), which comprises alternately administering an effective amount of 1) an estrogen receptor agonist or a salt thereof and 2) 1 or 2 compounds selected from an LHRH receptor agonist or antagonist and an antiestrogen drug, or a salt thereof;

(29) the method of the aforementioned (28), comprising changing the administration drug after a lapse of 3 months to 5 years;

(30) use of an androgen receptor agonist or a salt thereof for the production of an agent for the prophylaxis or treatment of bone metastatic prostate cancer;

(31) use of a non-steroidal androgen receptor agonist or a salt thereof for the prophylaxis or treatment of prostate cancer;

(32) use of an LHRH receptor agonist or antagonist or a salt thereof for the production of a pharmaceutical agent comprising 1) an LHRH receptor agonist or antagonist or a salt thereof in combination with 2) an androgen receptor agonist or a salt thereof; and

(33) use of an androgen receptor agonist or a salt thereof for the production of a pharmaceutical agent comprising 1) an LHRH receptor agonist or antagonist or a salt thereof in combination with 2) an androgen receptor agonist or a salt thereof; and the like.

The present invention moreover relates to (34) the method of any of the aforementioned (18), (19), (20), (21), (22), (23), (24) and (27), wherein the LHRH receptor agonist or antagonist is an LHRH receptor agonist;

(35) the method of the aforementioned (34), wherein the LHRH receptor agonist is leuprorelin;

(36) the method of any of the aforementioned (18), (19), (20), (21), (22), (23), (24) and (27), wherein the LHRH receptor agonist or antagonist is an LHRH receptor antagonist;

(37) the method of any of the aforementioned (18), (20), (22) and (24), wherein the androgen receptor agonist is a steroidal androgen receptor agonist;

(38) the method of the aforementioned (37), wherein the steroidal androgen receptor agonist is one or more compounds selected from the group consisting of dehydroepiandrosterone, testosterone, dihydrotestosterone, androstenedione, Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylestrenol and Norbolethone, or a salt thereof;

(39) the method of any of the aforementioned (18), (20), (22) and (24), wherein the androgen receptor agonist is a non-steroidal androgen receptor agonist;

(40) the method of any of the aforementioned (18), (20), (22) and (24), wherein the androgen receptor agonist or a salt thereof is administered in an amount of 0.001 mg to 2000 mg once or in plural doses a day;

(41) the method of any of the aforementioned (19), (21), (23) and (27), wherein the estrogen receptor agonist is a steroidal or non-steroidal estrogen receptor agonist;

(42) the method of any of the aforementioned (19), (21), (23) and (27), wherein the estrogen receptor agonist is one or more compounds selected from the group consisting of estradiol, estrone, estriol, stilbestrol, diethylstilbestrol and hexestrol, or a salt thereof; and the like.

BEST MODE FOR EMBODYING THE INVENTION

Figure 1:
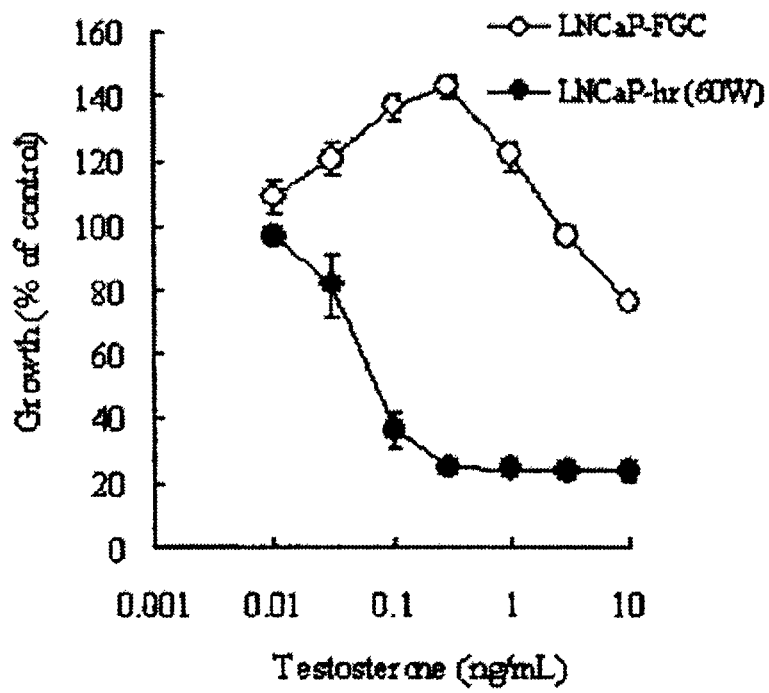
FIG. 1 shows cell growth rates of LNCaP-FGC and LNCaP-hr (highly androgen sensitive cell lines) cultured in the presence of testosterone, wherein the transverse axis shows testosterone concentration and the vertical axis shows cell growth rates.

The present invention is explained in detail in the following.

In the present invention, for example, the following are used as an LHRH receptor agonist or antagonist.

As the LHRH receptor agonist, for example, peptides described in *Treatment with LHRH analogs: Controversies and perspectives*, The Parthenon Publishing Group Ltd. (1996), JP-A-3-503165, JP-A-3-101695, JP-A-7-97334 and JP-A-8-259460 and the like are used. Specifically, for example, a peptide of the formula (SEQ ID NO: 1):

(Pyr)Glu-$R^1$-Trp-Ser-$R^2$-$R^3$-$R^4$-Arg-Pro-$R^5$ (I)

wherein $R^1$ is His, Tyr, Trp or p-$NH_2$-Phe; $R^2$ is Tyr or Phe; $R^3$ is Gly or D type amino acid residue optionally having substituents; $R^4$ is Leu, Ile or Nle; and $R^5$ is Gly-NH—$R^6$ ($R^6$ is a hydrogen atom or an alkyl group optionally having a hydroxyl group), NH—$R^7$ ($R^7$ is a hydrogen atom, an amino group, an alkyl group optionally having a hydroxyl group, or an ureido group (—NH—CO—$NH_2$)), or a salt thereof is used.

In the aforementioned formula (I), as the D type amino acid residue for $R^3$, for example, α-D-amino acid having up to 9 carbon atoms (e.g., D-Leu, Ile, Nle, Val, Nval, Abu, Phe, Phg, Ser, Thr, Met, Ala, Trp, α-Aibu) and the like are used. As the substituent for $R^3$, for example, tert-butyl, tert-butoxy, tert-butoxycarbonyl, methyl, dimethyl, trimethyl, 2-naphthyl, indolyl-3-yl, 2-methylindolyl, benzyl-imidazo-2-yl and the like are used. In the formula (I), as the alkyl group for $R^6$ or $R^7$, for example, a $C_{1-4}$ alkyl group is preferable, which is exemplified by methyl, ethyl, propyl, isopropyl, butyl, isobutyl, sec-butyl and tert-butyl.

In addition, as a salt of peptide represented by the formula (I) [hereinafter sometimes to be abbreviated as peptide (I)], for example, an acid salt (e.g., carbonate, bicarbonate, acetate, trifluoroacetate, propionate, succinate etc.) and a metal complex compound (e.g., copper complex, zinc complex etc.) are used. Peptide (I) or a salt thereof can be produced by a method described in, for example, U.S. Pat. Nos. 3,853,837, 4,008,209, 3,972,859, GB patent No. 1,423,083, Proceedings of the National Academy of Sciences of the United States of America, vol. 78, pp. 6509-6512 (1981) and the like or a method analogous thereto.

Peptide (I) is preferably any of the following formulas (a-(j).

(a) Leuprorelin, a peptide of the formula (I), wherein $R^1$=His, $R^2$=Tyr, $R^3$=D-Leu, $R^4$=Leu, $R^5$=NHCH$_2$—CH$_3$;

(b) Gonadrelin (SEQ ID NO: 2)

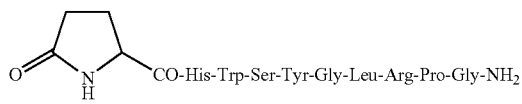

[DE Patent No. 2213737];

(c) Buserelin (SEQ ID NO: 3)

[U.S. Pat. No. 4,024,248, DE patent No. 2438352, JP-A-51-41359];

(d) Triptorelin (SEQ ID NO: 4)

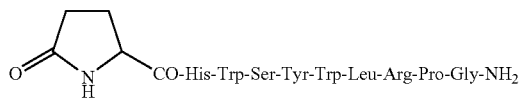

[U.S. Pat. No. 4,010,125, JP-A-52-31073];

(e) Goserelin (SEQ ID. NO: 5)

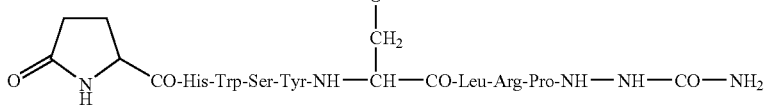

[U.S. Pat. No. 4,100,274, JP-A-52-136172];

(f) Nafarelin (SEQ ID NO: 6)

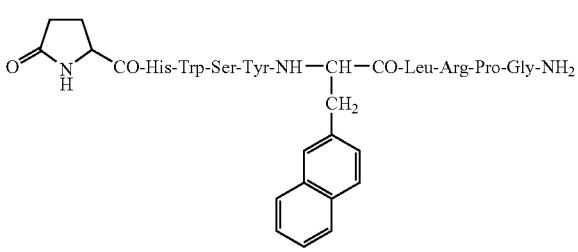

[U.S. Pat. No. 4,234,571, JP-A-55-164663, JP-A-63-264498, JP-A-64-25794];

(g) Histrelin (SEQ ID NO: 7)

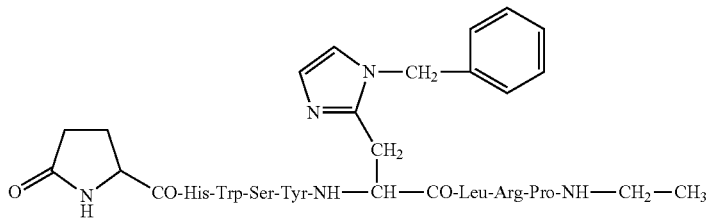

(h) Deslorelin (SEQ ID NO: 8)

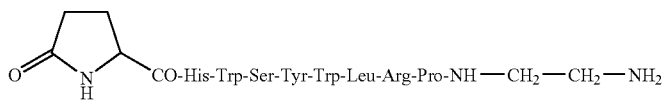

[U.S. Pat. No. 4,569,967, U.S. Pat. No. 4,218,439];

(i) Meterelin (SEQ ID NO: 9)

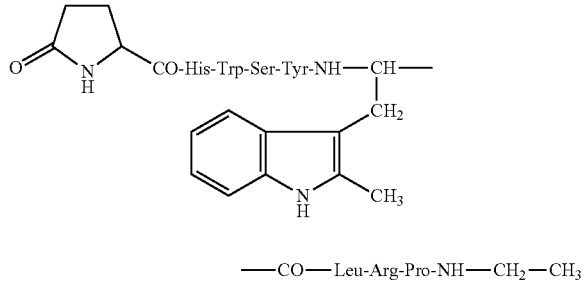

[WO 9118016];

(j) Lecirelin (SEQ ID NO: 10)

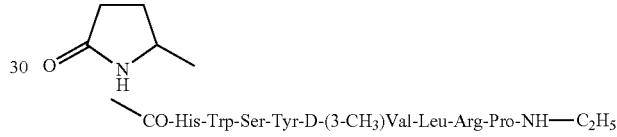

[BE patent No. 897455, JP-A-59-59654] and the like.

In the aforementioned formulas (c)-(j), an amino acid corresponding to $R^3$ in the formula (I) is a D-form. The peptide (I) or a salt thereof is particularly preferably leuprorelin or leuprorelin acetate. As used herein, leuprorelin acetate is an acetate of leuprorelin.

As the LHRH receptor antagonist, for example, those disclosed in U.S. Pat. Nos. 4,086,219, 4,124,577, 4,253,997 and 4,317,815, or a peptide represented by the formula:

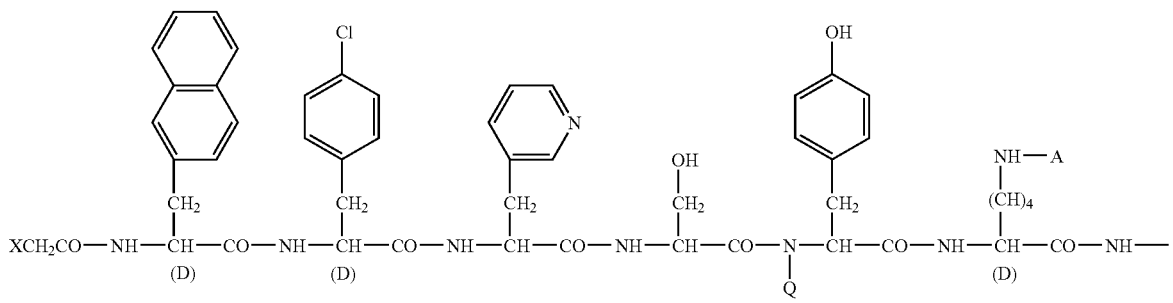

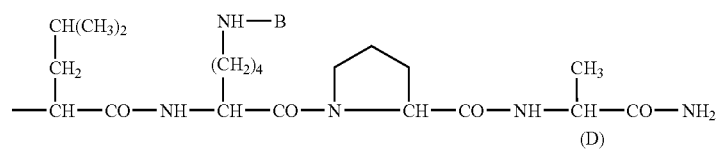

(II)

wherein X is a hydrogen or tetrahydrofurylcarboxamide, Q is a hydrogen or methyl, A is nicotinoyl or N,N'-diethylamidino and B is isopropyl or N,N'-diethylamidino [hereinafter sometimes to be abbreviated as peptide (II)] or a salt thereof are used. In the formula (II), X is preferably tetrahydrofurylcarboxamide, more preferably (2S)-tetrahydrofurylcarboxamide. A is preferably nicotinoyl. B is preferably isopropyl. When peptide (II) has one or more kinds of asymmetric carbon atoms, two or more kinds of optical isomers are present. Peptide (II) can be used as such optical isomer, or a mixture of these optical isomers.

As the salt of peptide (II), a pharmacologically acceptable salt is preferably used. As such salt, salts with inorganic acids (e.g., hydrochloric acid, sulfuric acid, nitric acid and the like), salts with organic acids (e.g., carbonic acid, bicarbonic acid, succinic acid, acetic acid, propionic acid, trifluoroacetic acid and the like) and the like are used. The salt of peptide (II) is more preferably a salt with an organic acid (e.g., carbonic acid, bicarbonic acid, succinic acid, acetic acid, propionic acid, trifluoroacetic acid and the like). The salt of peptide (II) is particularly preferably a salt with acetic acid. These salts may be a mono to tri salt.

The peptide (II) or a salt thereof preferably has the following formulas (1)-(4) (SEQ ID NOS 11-14, respectively in order of appearance).

—CONHCH$_2$COD2Nal-D4ClPhe-D3Pal-Ser-NMeTyr-DLys(Nic)-Leu-Lys(Nisp)-Pro-DAlaNH$_2$ (1)

—CONHCH$_2$COD2Nal-D4ClPhe-D3Pal-Ser-NMeTyr-DLys(Nic)-Leu-Lys(Nisp)-Pro-DAlaNH$_2$·m(CH$_3$COOH) (2)

wherein m is a real number of 1 to 3.
(3) NAcD2Nal-D4ClPhe-D3 Pal-Ser-Tyr-DhArg(Et$_2$)-Leu-hArg(Et$_2$)-Pro-DAlaNH$_2$
(4) NAcD2Nal-D4ClPhe-D3 Pal-Ser-Tyr-DhArg(Et$_2$)-Leu-hArg(Et$_2$)-Pro-DAlaNH$_2$·n(CH$_3$COOH)
wherein n is a real number of 1 to 3.

The aforementioned formulas (2) and (4) show salts or solvates. The peptide (II) or a salt thereof is more preferably the aforementioned (1) or (2), which is particularly preferably an S-isomer.

The peptide (II) or a salt thereof can be produced by a known method, such as a method described in JP-A-3-101695 (EP-A 413209), Journal of Medicinal Chemistry, vol. 35, p. 3942 (1992) and the like, or a method analogous thereto.

Furthermore, it is possible to use a linear peptide which is a derivative of LHRH (U.S. Pat. No. 5,140,009, U.S. Pat. No. 5,171,835), a cyclic hexapeptide derivative (JP-A-61-191698), a bicyclic peptide derivative (Journal of Medicinal Chemistry, vol. 36, pp. 3265-3273 (1993)) and the like. As the non-peptide compound having an LHRH antagonistic action, compounds described in JP-A-62-116514, WO 95/28405 (JP-A-8-295693), WO 97/14697 (JP-A-9-169767), WO 97/14682 (JP-A-9-169735), WO 96/24597 (JP-A-9-169768) and the like, J. Med. Chem., vol. 32, pp. 2036-2038 (1989), and the like can be used.

As the LHRH receptor antagonist, abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidine-2,4 (1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4 (1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4 (1H,3H)-dione hydrochloride and the like are used particularly preferably.

As the androgen receptor agonist, a steroidal androgen receptor agonist and a non-steroidal androgen receptor agonist can be used.

As the steroidal androgen receptor agonist, endogenous androgens such as dehydroepiandrosterone, testosterone, dihydrotestosterone (DHT), androstenedione and the like, synthetic androgens (Anabolic steroid) such as Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylstrenol, Norbolethone and the like, and the like can be used.

As the non-steroidal androgen receptor agonist, LGD-2226 and the like can be used.

As the androgen receptor agonist, the aforementioned compounds alone or 2 or more compounds in combination can be used, with preference given to testosterone, dihydrotestosterone and the like.

As the estrogen receptor agonist, steroidal estrogen receptor agonists such as estradiol, estrone, estriol and the like; and synthetic estrogen (non-steroidal estrogen) receptor agonists such as stilbestrol, diethylstilbestrol, hexestrol and the like can be used.

As the estrogen receptor agonist, the aforementioned compounds alone or 2 or more compounds in combination can be used, with preference given to estradiol, diethylstilbestrol and the like.

As the non-steroidal estrogen receptor agonist, tamoxifen citrate, toremifene citrate; raloxifene, arzoxifene, lasofoxifene, TSE-424, SERM-3339, SPC-8490 and the like can be used.

In the present invention, the mode of administration of the pharmaceutical agent (hereinafter to be sometimes abbreviated as combination agent of the present invention) for combined use of an LHRH receptor agonist or antagonist or a salt thereof with an androgen receptor agonist or a salt thereof is not particularly limited, as long as an LHRH receptor agonist or antagonist is combined with an androgen receptor agonist when administered. Examples of such administration mode include (1) administration of a single preparation obtained by simultaneous formulation of an LRRH receptor agonist or antagonist and an androgen receptor agonist, (2) simultaneous administration by the same administration route of two kinds of preparations obtained by separate formulation of an LHRH receptor agonist or antagonist and an androgen receptor agonist, (3) staggered administration by the same administration route of two kinds of preparations obtained by separate formulation of an LHRH receptor agonist or antagonist and an androgen receptor agonist, (4) simultaneous administration by different administration routes of two kinds of preparations obtained by separate formulation of an LHRH receptor agonist or antagonist and an androgen receptor agonist, (5) staggered administration by different administration routes of two kinds of preparations obtained by separate formulation of an LHRH receptor agonist or antagonist and an androgen receptor agonist, such as administration in the order of an LHRH receptor agonist or antagonist and then an androgen receptor agonist, or in the reversed order, and the like.

As the antiandrogen drug and antiestrogen drug, steroidal or non-steroidal antiandrogen agents and antiestrogen agents can be used.

As the antiandrogen drug, for example, flutamide, bicalutamide, nilutamide and the like can be used, and as the antiestrogen drug, for example, tamoxifen citrate, toremifene citrate; SERM agents (selective estrogen receptor modulator) such as raloxifene, arzoxifene, lasofoxifene, TSE-424, SERM-3339 or SPC-8490 and the like; and ER down regulator and the like can be used. Furthermore, the following pharmaceutical agents known to have an antiandrogen or antiestrogen action and the like can be used.

As the antiandrogen drug and antiestrogen drug in the present application, moreover, for example, fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, mepitiostane, testrolactone, aminoglutethimide, droloxifene, epitiostanol, ethynylestradiol sulfonate, aromatase inhibitors (e.g., fadrozole hydrochloride, anastrozole, letrozole, Excemestane, vorozole, formestane, finzorole and the like), 5α-reductase inhibitors (e.g., 5α-reductase 2 inhibitors such as finasteride, epristeride, dutasteride, izonsteride and the like; 5α-reductase 1 inhibitors such as a compound described in WO 93/23420, a compound described in WO 95/11254, 4,7β-dimethyl-4-aza-5α-cholestan-3-one, 3-oxo-4-aza-4,7β-dimethyl-16β-(4-chlorophenoxy)-5α-androstane, 3-oxo-4-aza-4,7β-dimethyl-16β-(phenoxy)-5α-androstane and the like; 5α-reductase 1 and 5α-reductase 2 double inhibitors such as a compound described in WO 95/07927, 3-oxo-4-aza-17β-(2,5-trifluoromethylphenyl-carbamoyl)-5α-androstane and the like; and the like), adrenocortical hormone pharmaceutical agents (e.g., dexamethasone, prednisolone, betamethasone, triamcinolone and the like), androgen synthesis inhibitors (e.g., abiraterone, ketoconazole, 17α-hydroxylase/$C_{17-20}$ lyase inhibitor (as the $C_{17,20}$ lyase inhibitors, steroidal compounds and non-steroidal compounds can be used. As the steroidal compounds, for example, the compounds described in WO 92/15404, WO 93/20097, EP-A288053, EP-A413270 and the like can be used, and as the non-steroidal compounds, for example, (1H-imidazol-1-yl)methyl substituted benzimidazole derivative disclosed in JP-A-64-85975, carbazole derivatives disclosed in WO 94/27989, WO 96/14090 and WO 97/00257, azole derivative disclosed in WO 95/09157, 1H-benzimidazole derivative disclosed in U.S. Pat. No. 5,491,161, dihydronaphthalene derivative disclosed in WO 99/18075, compounds described in WO 98/37070, WO 99/54309, WO 00/78727, WO 01/30763, WO 01/30762, WO 01/30764 and the like can be used) and the like), pharmaceutical agents that delay retinoid and metabolism of retinoid (e.g., liarozole and the like), and the like can be used.

As the antiandrogen agent, preferred are bicalutamide, flutamide and the like.

As the antiestrogen drug, preferred are tamoxifen, toremifene, anastrozole, letrozole and the like.

Specific examples of the hormone-dependent disease include sex hormone dependent cancers (e.g., prostate cancer, uterine cancer, breast cancer, pituitary gland tumor and the like), prostatic hypertrophy, endometriosis, hysteromyoma, precocious puberty, dysmenorrhea, amenorrhea, premenstrual syndrome, multilocular ovarian syndrome, postoperative recurrence of the aforementioned cancers, dwarfism, Alzheimer's disease, climacteric disturbance, indefinite complaints, metastasis of the aforementioned cancers, sex hormone-dependent diseases such as calcium•phosphorus bone metabolism disorder and the like and contraception (or infertility when a rebound effect after drug withdrawal is utilized), benign or malignant tumor which is sex hormone non-dependent but LHRH sensitive, and the like can be mentioned.

While the pharmaceutical agent of the present invention can be used for the prophylaxis or treatment of the aforementioned hormone-dependent diseases, it is particularly preferably used for the prophylaxis or treatment of sex hormone-dependent cancer, more preferably for the prophylaxis or treatment of prostate cancer (including lymph metastatic prostate cancer and bone metastatic prostate cancer), uterine cancer and breast cancer.

The object of treating cancer naturally means disappearance and cure of a malignant tumor, which includes reduction and maintenance of the volume of a malignant tumor and the like. Such treatment objects are appropriately determined in medical situations.

Mammal refers to vertebrata that is warm-blooded and lung-breathing and includes, for example, human, simian, mouse, rat, swine, bovine, sheep, dog, horse and the like.

The bone metastatic prostate cancer refers to a malignant tumor that spreads to a bone tissue where, for example, MDA PCa 2b has been established.

Production Method of Highly Androgen Sensitive Prostate Cancer Cell

A prostate cancer cell highly sensitive to androgen can be obtained by culturing prostate cancer cell (e.g., LNCaP-FGC and MDA PCa 2b cell lines (these are available from the ATCC) and the like) in a culture medium containing a charcoal treated serum. Culture is preferably continued for 3-8 months.

Production Method of Highly Estrogen Sensitive Breast Cancer Cell & Uterine Cancer Cell In the same manner, a breast or uterine cancer cell highly sensitive to estrogen can be obtained by culturing a breast or uterine cancer cell (e.g., MCF-7 cell line (these are available from the ATCC) and the like) in a culture medium containing a charcoal treated serum. Culture is preferably continued for 3-8 months.

The androgen sensitivity of cancer cell can be measured by determining the reactivity of cancer cell to an androgen receptor agonist.

To be specific, it can be measured by culturing the cancer cell in the presence of an androgen. When the growth of cancer cell is promoted in an environment corresponding to normal testosterone concentration in living organisms (though subject to change depending on the measurement method, for example, 2.5-11 ng/ml: Guide to clinical examination '95, Bunkodo), it is assumed to be typical sensitivity, and when the growth of cancer cell is suppressed in this environment or the growth is promoted in an environment corresponding to the testosterone concentration during sterilization, it is assumed that the androgen sensitivity is enhanced.

In the same manner, the estrogen sensitivity of cancer cell can be measured by determining the reactivity of cancer cell to an estrogen receptor agonist.

To be specific, it can be measured by culturing the cancer cell in the presence of an estrogen. When the growth of cancer cell is promoted in an environment corresponding to normal estrogen concentration in living organisms (though subject to change depending on the measurement method, for example, 20-500 pg/ml in the case of estradiol: Guide to clinical examination '95, Bunkodo), it is assumed to be typical sensitivity, and when the growth of cancer cell is suppressed in this environment or the growth is promoted in an environment corresponding to the estrogen concentration during menopause, it is assumed that the estrogen sensitivity is enhanced.

It is also possible to determine (e.g., indirectly by increase or decrease of cancer cell growth) sensitivity to sex hormones (androgen and estrogen) of cancer cell by conventional diagnosis methods of prostate cancer, breast cancer and uterine cancer (e.g., Garnick, M., Scientific American, 270, p 72-81, 1994; Garnick, M, Annals of Internal Medicine, 118, p 803-818, 1993). As generally practiced, the important information to determine the timing of change in the administration of a pharmaceutical agent and the like can be decided by determining a therapeutic effect based on the measurement of the size and the like of prostate (tumor), breast tumor and uterine tumor, by rectal test, palpation, ultrasonic test, magnetic resonance imaging (MRI), X ray, intravenous pyelography, CAT scanning, biopsy and the like.

In addition, the progress of prostate cancer can be easily determined by detecting PSA (prostatic specific antigen), which is a prostate specific antigen.

In the present invention, when an LHRH receptor agonist or antagonist and an androgen receptor agonist are used in combination, when an androgen receptor agonist, and 1 or 2 compounds selected from an LHRH receptor agonist or antagonist and an antiandrogen drug or a salt thereof are used in combination, when an estrogen receptor agonist, and 1 or 2 compounds selected from an LHRH receptor agonist or antagonist and an antiestrogen drug or a salt thereof are used in combination, when an androgen receptor agonist is administered as an agent for the prophylaxis or treatment of bone metastatic prostate cancer, and when a non-steroidal androgen receptor agonist is administered as an agent for the prophylaxis or treatment of prostate cancer, each drug is administered in the following amounts, which can be used in an appropriately increased or decreased amount depending on the pharmaceutical agent to be used in combination, dosage form, condition, administration period and the like, and which can be administered once a day or in several portions a day.

In the present invention, a single dose of the LHRH receptor agonist can be appropriately selected from the range of, for example, about 0.01 mg to 100 mg/kg body weight, preferably about 0.02 mg to 50 mg/kg body weight, more preferably 0.05 mg to 20 mg/kg body weight.

When the above-mentioned preparation is administered as an injection for an adult patient (body weight 60 kg), an LHRH receptor agonist is subcutaneously or intramuscularly administered in a single dose of generally about 0.01 to about 50 mg, preferably about 0.1 to about 20 mg, more preferably about 0.1 to about 15 mg. In addition, when an injection comprising a sustained-release microcapsule comprising the above-mentioned LHRH receptor agonist is administered, the dose varies depending on the drug release period of a sustained-release microcapsule. For example, for administration of once in about 1 month for an adult patient (body weight 60 kg), a single dose of generally about 0.01 to about 20 mg, preferably about 0.1 to about 10 mg, more preferably about 0.1 to about 5 mg, of an LHRH receptor agonist is subcutaneously or intramuscularly administered. For example, for administration of once in about 3 months for an adult patient (body weight 60 kg), a single dose of generally about 0.1 to about 30 mg, preferably about 0.1 to about 20 mg, more preferably about 1 to about 15 mg, of an LHRH receptor agonist is subcutaneously or intramuscularly administered.

The dose of an LHRH receptor antagonist is preferably about 1-3000 µg/kg/day, more preferably about 1-2000 µg/kg/day, more preferably about 1-1000 µg/kg/day.

The dose of an androgen receptor agonist is 0.001 mg-2000 mg/kg/day, preferably about 0.01-500 mg, more preferably about 0.01-100 mg, which is generally administered in 1 to 4 portions a day.

The dose of an estrogen receptor agonist is 0.001 mg-2000 mg/kg/day, preferably about 0.01-500 mg, more preferably about 0.01-100 mg, which is generally administered in 1 to 4 portions a day.

The dose of an antiandrogen drug is 0.001 mg-2000 mg/kg/day, preferably about 0.01-500 mg, more preferably about 0.01-100 mg, which is generally administered in 1 to 4 portions a day.

The dose of an antiestrogen drug is 0.001 mg-2000 mg/kg/day, preferably about 0.01-500 mg, more preferably about 0.01-100 mg, which is generally administered in 1 to 4 portions a day.

While subject to change depending on the dosage form, administration method, carrier and the like, the pharmaceutical agent of the present invention can be produced by adding an LHRH receptor agonist or antagonist, an androgen receptor agonist, an estrogen receptor agonist, an antiandrogen drug or antiestrogen drug and the like in generally 0.1-95% (w/w) of the total amount of the preparation according to a conventional method.

In addition, by combining 1 to 3 kinds selected from the group consisting of (1) administering an effective amount of the pharmaceutical agent of the present invention, (2) (i) administering an effective amount of other anticancer agents, (ii) administering an effective amount of other hormone therapy agents, and (iii) therapies without medicine, cancer can be more effectively prevented or treated. As the therapy without medicine, for example, operation, radiation therapy, gene therapy, thermotherapy, cryotherapy, laser cauterization therapy and the like can be mentioned, and two or more of these can be combined.

For example, the compound of the present invention can be used in combination with other hormone therapy agents, anticancer agents (e.g., chemotherapy agent, immunotherapy agent and pharmaceutical agent inhibiting the action of cell growth factor and receptor thereof) and the like (hereinafter to be briefly referred to as combination drug) [hereinafter to be briefly referred to as combination agent].

While the compound of the present invention shows a superior anticancer effect even when used as a single agent, when it is used in combination with one or more of the above-mentioned combination drugs (combined use of plural agents), the effect can be reinforced furthermore.

In addition, the pharmaceutical agent of the present invention or the combination agent of the present invention may be combined with a therapy without medicine, such as (1) operation, (2) vasopressor chemotherapy using angiotensin II, (3) gene therapy, (4) thermotherapy, (5) cryotherapy, (6) laser cauterization therapy, (7) radiation therapy and the like.

For example, the use of the pharmaceutical agent of the present invention or the combination agent of the present invention before or after operation and the like, or before or after a combined treatment of two or three kinds thereof affords effects such as prevention of expression of resistance, prolonged Disease-Free Survival time, suppression of metastasis or recurrence, life prolonging and the like.

It is also possible to combine a therapy with the pharmaceutical agent of the present invention or the combination agent of the present invention, with a supportive therapy such as (i) administration of antibiotics (e.g., β-lactam group such as pansporin, macrolide group such as clarithromycin etc.) against complication with various infectious diseases, (ii) administration of total parenteral nutrition, amino acid preparation, multivitamin preparation for improvement of malnutrition, (iii) administration of morphine for relieving pain, (iv) administration of medicine to improve side effects such as nausea, vomit, anorexia, diarrhea, hypoleukocytemia, thrombocytopenia, decreased hemoglobin concentration, alopecia, hepatopathy, nephropathy, DIC, onset of fever and the like, and (v) administration of medicine to suppress multiple drug resistance in cancer, and the like.

It is preferable that the pharmaceutical agent of the present invention or an agent for the prophylaxis or treatment of the present invention be administered before or after the aforementioned treatment by oral administration (inclusive of sustained release administration), intravenous administration (inclusive of bolus, infusion and inclusion compound), subcutaneous or intramuscular injection (inclusive of bolus, infusion, sustained release administration), transdermal, intratumor and proximal administrations.

When the pharmaceutical agent of the present invention or the combination agent of the present invention is administered before operation and the like, for example, it may be administered once in about 30 min. to 24 hrs. before the operation and the like, or may be administered in 1 to 3 cycles in about 3 to 6 months before the operation and the like. The administration of the pharmaceutical agent of the present invention or the combination agent of the present invention before operation and the like can, for example, shrink cancer tissues, thereby facilitating the operation and the like.

When the pharmaceutical agent of the present invention or the combination agent of the present invention is administered after operation and the like, it may be administered repeatedly in about 30 min to 24 hrs. after the operation and the like, for example, for several weeks to 3 months. The administration of the pharmaceutical agent of the present invention or the combination agent of the present invention after operation and the like enhances the effect of the operation and the like.

The treatment method of the present invention includes
(1) a method for treating prostate cancer, which comprises administering an effective amount of an LHRH receptor agonist or antagonist or a salt thereof to a mammal, and after prostate cancer cell has become highly sensitive to androgen, administering an effective amount of an androgen receptor agonist or a salt thereof,
(2) a method for treating prostate cancer, which comprises administering an effective amount of an LHRH receptor agonist or antagonist or a salt thereof in combination with an effective amount of an androgen receptor agonist or a salt thereof to a mammal,
(3) a method for treating prostate cancer, which comprises administering an effective amount of an LHRH receptor agonist or antagonist or a salt thereof in combination with an effective amount of an androgen receptor agonist or a salt thereof to a mammal to shrink a prostate tumor, and then performing a surgery or radiation treatment,
(4a)1) a method for treating prostate cancer, which comprises 1) administering an androgen receptor agonist or a salt thereof to a highly androgen sensitive prostate cancer cell for a certain time period, 2) thereafter when the androgen sensitivity of the cancer cell has become lower, administering an effective amount of 1 or 2 compounds selected from an LHRH receptor agonist or antagonist and an antiandrogen drug, or a salt thereof, or when the androgen sensitivity of the cancer cell has increased, administering an effective amount of an androgen receptor agonist or a salt thereof, and 3) repeating the step 2) as necessary until an object of cancer treatment is achieved;
(4b) the method of the aforementioned (4a), which comprises alternately administering an effective amount of 1) an androgen receptor agonist or a salt thereof and 2) 1 or 2 compounds selected from an LHRH receptor agonist or antagonist and an antiandrogen drug or a salt thereof; and
(4c) the method of the aforementioned (4b), which comprises changing the administration drug after a lapse of 3 months to 5 years.

By administering an effective amount of an LHRH receptor agonist or antagonist or a salt thereof for a certain period (e.g., 3 months to 5 years), androgen sensitivity of the prostate cancer cell is enhanced. Thereafter, by administering an effective amount of an androgen receptor agonist or a salt thereof, the growth of the prostate cancer cell can be suppressed or the tumor can be shrunk. When administration of the androgen receptor agonist is continued and the androgen sensitivity of the prostate cancer cell returns to the level of normal cells or the prostate tumor starts to grow (tumor volume and the like increased), a most suitable treatment of prostate cancer can be performed by changing to an administration of 1 or 2 compounds selected from an LHRH receptor agonist or antagonist and an antiandrogen drug, or a salt thereof, after which selecting based on such androgen sensitivity of the cancer cell and changing to an administration of 1 or 2 compounds selected from an LHRH receptor agonist or antagonist and an antiandrogen drug, or a salt thereof (when androgen sensitivity of the cancer cell is of the same level as normal cells [e.g., LNCaP 104-S cell (Cancer Res, 54, p 1566-1573), LNCaP-FGC cell and the like]) or an administration of androgen receptor agonist or a salt thereof (when androgen sensitivity of the cancer cell is higher than normal cells [e.g., LNCaP 104-R2 cell (*Cancer Res*, 54, pp. 1566-1573), LNCaP-hr cell and the like]).

The timing of changing these administrations can be appropriately set for each treatment, and, for example, from 3 months to 5 years, preferably from 6 months to 4 years, more preferably from 1 year to 3 years, still more preferably from 1 year to 2 years.

Therefore, when MAB (Maximum androgen blockade) therapy and the like is performed for a certain period by the administration of LHRH receptor agonist or antagonist (e.g., LHRH receptor agonist and the like) and the like, the androgen sensitivity of prostate cancer cell is highly likely to have been enhanced, and a treatment method based on a combined use of the androgen receptor agonist or a salt thereof of the present invention proves effective. In this case, an androgen receptor agonist can be administered while continuing the administration of an LHRH receptor agonist or antagonist (whereby a condition similar to an intermittent therapy with LHRH receptor agonist or antagonist can be performed while continuing administration of an LHRH receptor agonist or antagonist), or administration of an LHRH receptor agonist or antagonist may be stopped and changed to the administration of an androgen receptor agonist. Both cases are encompassed in the present invention.

While the androgen sensitivity of prostate cancer cell can be measured by the aforementioned method for determining the reactivity with androgen, it can be also assumed based on the increase or decrease of tumor marker, physiological index, tumor volume and the like under administration of a certain drug.

In addition, the treatment method of the present invention includes (5) a method for treating breast cancer or uterine cancer, which comprises administering an effective amount of an LHRH receptor agonist or antagonist or a salt thereof to a mammal, and after breast cancer or uterine cancer cell has become highly sensitive to estrogen, administering an effective amount of an estrogen receptor agonist or a salt thereof;

(6) a method for treating breast cancer or uterine cancer, which comprises administering an effective amount of an LHRH receptor agonist or antagonist or a salt thereof in combination with an effective amount of an estrogen receptor agonist or a salt thereof to a mammal;

(7) a method for treating breast cancer or uterine cancer, which comprises administering an effective amount of an LHRH receptor agonist or antagonist or a salt thereof in combination with an effective amount of an estrogen receptor agonist or a salt thereof to a mammal to shrink breast tumor or uterine tumor, and then performing a surgery or radiation treatment;

(8a) a method for treating breast cancer or uterine cancer, which comprises 1) administering an estrogen receptor agonist or a salt thereof to a highly estrogen sensitive breast cancer or uterine cancer cell for a certain time period, 2) thereafter when the estrogen sensitivity of the cancer cell has become lower, administering an effective amount of 1 or 2 compounds selected from an LHRH receptor agonist or antagonist and an antiestrogen drug, or a salt thereof, or when the estrogen sensitivity of the cancer cell has increased, administering an effective amount of an estrogen receptor agonist or a salt thereof, and 3) repeating the step 2) as necessary until an object of cancer treatment is achieved;

(8b) the method of the aforementioned (8a), which comprises alternately administering an effective amount of 1) an estrogen receptor agonist or a salt thereof and 2) 1 or 2 compounds selected from an LHRH receptor agonist or antagonist and an antiestrogen drug, or a salt thereof; and (8c) the method of the aforementioned (8b), comprising changing the administration drug after a lapse of 3 months to 5 years.

In the same manner as above, by administering an effective amount of an LHRH receptor agonist or antagonist or a salt thereof for a certain period (e.g., 3 months to 5 years), estrogen sensitivity of the breast or uterine cancer cell is enhanced. Thereafter, by administering an effective amount of an estrogen receptor agonist or a salt thereof, the growth of the breast or uterine cancer cell can be suppressed or the tumor can be shrunk. When administration of the estrogen receptor agonist is continued and the estrogen sensitivity of the breast or uterine cancer cell returns to the level of normal cells or the breast or uterine tumor starts to grow (tumor volume and the like increased), a most suitable treatment of breast or uterine cancer can be performed by changing to an administration of 1 or 2 compounds selected from an LHRH receptor agonist or antagonist and an antiestrogen drug, or a salt thereof, after which selecting based on such estrogen sensitivity of the cancer cell and changing to an administration of 1 or 2 compounds selected from an LHRH receptor agonist or antagonist and an antiestrogen drug, or a salt thereof (when estrogen sensitivity of cancer cell is of the same level as normal cells) or an administration of estrogen receptor agonist or a salt thereof (when estrogen sensitivity of the cancer cell is higher than normal cells).

The timing of changing these administrations can be appropriately set for each treatment, and, for example, from 3 months to 5 years, preferably from 6 months to 4 years, more preferably from 1 year to 3 years, still more preferably from 1 year to 2 years.

Therefore, when LHRH receptor agonist or antagonist (e.g., LHRH receptor agonist and the like) and the like are administered for a certain period, the estrogen sensitivity of breast or uterine cancer cell is highly likely to have been enhanced, and a treatment method based on a combined use of the estrogen receptor agonist or a salt thereof of the present invention proves effective. In this case, an estrogen receptor agonist can be administered while continuing the administration of an LHRH receptor agonist or antagonist, or administration of an LHRH receptor agonist or antagonist may be stopped and changed to the administration of an estrogen receptor agonist. Both cases are encompassed in the present invention.

While the estrogen sensitivity of breast or uterine cancer cell can be measured by the aforementioned method for determining the reactivity with estrogen, it can be also assumed based on the increase or decrease of tumor marker, physiological index, tumor volume and the like under administration of a certain drug.

The aforementioned LHRH receptor agonist or antagonist (e.g., LHRH receptor agonist, preferably leuprorelin or a salt thereof, more preferably leuprorelin acetate) can be administered orally as a tablet sugar coated as necessary, a capsule, an elixir, a sustained-release preparation and the like, or parenterally in the form of an injection such as a sterile solution, a suspension, a sustained-release preparation (particularly a sustained-release microcapsule) and the like with water or other pharmacologically acceptable solution, an embedded agent (a formed product with a biodegradable polymer as a base, one that is sealed in a tube of a biologically compatible metal such as titanium and the like and releases the active ingredient at a predetermined speed), an injection wherein a biodegradable polymer and a drug are dissolved or dispersed in an organic solvent administrable to living organisms, or a transnasal administration preparation of a solution, a suspension and the like. It is preferably administered as a sustained-release preparation, particularly preferably as a sustained-release injection. When the sustained-release preparation is a sustained-release microcapsule, it is preferably a long-term sustained-release microcapsule that releases an LHRH receptor agonist or antagonist over the period of 2 months or longer.

The aforementioned preparation can be produced by admixing leuprorelin or a salt thereof, more preferably leuprorelin acetate with a physiologically known carrier, flavor, excipient, vehicle, preservative, stabilizer, binder and the like in a unit dosage form required for generally admitted preparation practice.

As the additive that can be admixed and contained in a tablet, a capsule and the like, for example, binders such as gelatin, cornstarch, tragacanth and gum arabic, excipients such as crystalline cellulose, swelling agents such as cornstarch, gelatin, alginic acid and the like, lubricants such as magnesium stearate, sweeteners such as sucrose, lactose and saccharin, flavors such as peppermint, akamono oil and cherry, and the like can be used. When the unit dosage form is a capsule, the aforementioned type of materials can further contain a liquid carrier such as fats and oils. A sterile composition for injection can be produced according to conventional preparation practice such as dissolving or suspending an active substance, naturally occurring vegetable oil such as sesame oil, palm oil and the like, and the like in a vehicle such as water for injection, and the like. As an aqueous solution for injection, for example, isotonic solutions (e.g., D-sorbitol, D-mannitol, sodium chloride and the like) containing physiological saline, glucose and other auxiliary drugs and the like are used, which may be used concurrently with suitable dissolution aids, such as alcohol (e.g., ethanol), polyalcohol (e.g., propylene glycol, polyethylene glycol), non-ionic surfactants (e.g., polysorbate 80™, HCO-50) and the like. As an oily solution, for example, sesame oil, soybean oil and the like are used, which may be used concurrently with dissolution aids such as benzyl benzoate, benzyl alcohol and the like.

Furthermore, the aforementioned preparation may be blended with, for example, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like), antioxidants and the like. A prepared injection solution is generally filled in a suitable hermetic container such as ampoule, vial and the like.

A sustained-release preparation (particularly a sustained-release microcapsule) containing the aforementioned LHRH receptor agonist or antagonist (preferably leuprorelin or a salt thereof, more preferably leuprorelin acetate) can be produced according to a known method such as a method described in, for example, JP-A-60-100516, JP-A-62-201816, JP-A-4-321622, JP-A-6-192068, JP-A-9-132524, JP-A-9-221417, JP-A-11-279054, WO 99/360099 and the like.

Of the aforementioned sustained-release preparations, "a long-term sustained-release microcapsule designed for zero order release of a physiological active substance over 2 months or longer" described in JP-A-4-321622 is particularly preferably used.

One example of the production method of the aforementioned sustained-release microcapsule is described in the following.

First, an LHRH receptor agonist or antagonist (preferably leuprorelin or a salt thereof, more preferably leuprorelin acetate) is dissolved in water at about 20% to 70% (W/W), preferably 25-65% (W/W), more preferably 35-60% (W/W), and, if necessary, gelatin, or a drug retaining substance such as basic amino acid and the like is dissolved or suspended therein to give an internal aqueous phase.

The internal aqueous phase may be supplemented with a pH regulator for retaining stability or solubility of an LHRH receptor agonist or antagonist (e.g., LHRH receptor agonist, preferably leuprorelin or a salt thereof, more preferably leuprorelin acetate), such as carbonic acid, acetic acid, oxalic acid, citric acid, phosphoric acid, hydrochloric acid, sodium hydroxide, arginine, lysine or a salt thereof. In addition, as a stabilizer for an LHRH receptor agonist or antagonist (e.g., LHRH receptor agonist, preferably leuprorelin or a salt thereof, more preferably leuprorelin acetate), albumin, gelatin, citric acid, sodium ethylenediaminetetraacetate, dextrin, sodium hydrogen sulfite, polyol compounds such as polyethylene glycol and the like, or p-oxybenzoic acid esters (methylparaben, propylparaben and the like) conventionally used as preservatives, benzyl alcohol, chlorobutanol, thimerosal and the like may be added.

The internal aqueous phase thus obtained is added to a solution (oil phase) containing a polymer and emulsified to give a W/O emulsion. For this emulsifying operation, a known dispersing method is used, and, for example, an intermittent shaking method, a method using a mixer such as a propeller stirrer, a turbine stirrer and the like, a colloidal mill method, a homogenizer method, an ultrasonication method and the like are used.

Then, thus-prepared W/O emulsion is subjected to microcapsulation step. For this step, an in-water drying method or a phase separation method can be applied. When a microcapsule is prepared by a an in-water drying method, the W/O emulsion is further added to a third aqueous phase to form a W/O/W three-phase emulsion and a solvent in the oily phase is evaporated to give a microcapsule.

An emulsifier may be added to the aforementioned external aqueous phase, and an example thereof may be any as long as it forms a generally stable O/W emulsion. For example, anion surfactants (sodium oleate, sodium stearate, sodium lauryl sulfate and the like), non-ionic surfactants (sorbitan polyoxyethylene fatty acid ester [Tween 80, Tween 60, Atlas Powder], polyoxyethylene castor oil derivatives [HCO-60, HCO-50, Nikko Chemicals] and the like), or polyvinylpyrrolidone, polyvinyl alcohol, carboxymethyl cellulose, lecithin, gelatin and the like can be mentioned, wherein one or more kinds thereof may be used in combination. The concentration during use is appropriately selected from the range of about 0.01% to 20%, more preferably about 0.05% to 10%.

For evaporation of the solvent from an oily phase, a method generally used is employed. Such method includes gradual depressurization while stirring with a propeller stirrer, magnetic stirrer and the like, or evaporation using a rotary evaporator and the like while controlling the degree of vacuum. In this case, at a time point when solidification of a polymer has proceeded to a certain degree, a W/O/W emulsion is gradually heated to more completely perform desorption of the solvent, whereby the necessary time can be shortened.

The microcapsule thus obtained is subjected to centrifugal separation or filtration and separated, and free LHRH receptor agonist or antagonist (preferably leuprorelin or a salt thereof, more preferably leuprorelin acetate), a drug retaining substance, an emulsifier and the like adhered to the surface of microcapsule are repeatedly washed several times with distilled water, dispersed again in distilled water and the like and lyophilized. At this time, a coagulation preventive (e.g., mannitol, sorbitol, lactose, glucose and the like) may be added. Heating is applied if necessary, whereby water and organic solvent in microcapsule is more completely removed under reduced pressure.

For producing microspheres by the phase separation method, a coacervating agent is gradually added to the w/o emulsion while the emulsion is stirred, to precipitate and solidify a polymer.

Any coacervating agent can be used, as long as it is a polymeric, mineral oil or vegetable oil compound miscible with the solvent for a polymer and that does not dissolve a polymer for capsulation. Examples of such coacervating agents include silicon oil, sesame oil, soybean oil, corn oil, cotton seed oil, coconut oil, linseed oil, mineral oil, n-hexane and n-heptane. Two or more of these may be used in combination.

The microcapsule thus obtained is filtrated, separated, washed repeatedly with heptane and the like and a coacervating agent is removed. A free drug is removed by a method similar to an in-water drying method and the solvent is eliminated. A coagulation preventive may be added to prevent coagulation of particles during washing.

The microcapsule obtained above is lightly pulverized, if necessary, passed through a sieve, thereby removing microcapsules having large sizes. The particle size of the microcapsule is desirably in the range of about 0.5-1000 μm in an average diameter, more preferably in the range of about 2-500 μm. When the microcapsule is used as a suspension, the range may be any as long as it can be dispersed and pass through a needle. For example, it is desirably in the range of about 2 to 100 μm.

The aforementioned polymer include, for example, biodegradable polymers such as polymers and copolymers that have been synthesized from one or more kinds of α-hydroxycarboxylic acids selected from α-hydroxymonocarboxylic acids (e.g., glycolic acid, lactic acid), α-hydroxydicarboxylic acids (e.g., malic acid), α-hydroxytricarboxylic acids (e.g., citric acid) etc., and that have a free carboxyl group, or mixtures thereof; poly-α-cyanoacrylic acid esters; polyamino acids (e.g., poly-γ-benzyl-L-glutamic acid); and maleic anhydride copolymers (e.g., styrene-maleic acid copolymers).

The mode of monomer binding may be random, block, or graft. When the above-mentioned α-hydroxymonocarboxylic acids, α-hydroxydicarboxylic acids, and α-hydroxytricarboxylic acids have an optically active center in their molecular structures, they may be of the D-, L- or DL-configuration. Of these, lactic acid-glycolic acid polymers [hereinafter also referred to as poly(lactide-co-glycolide), poly(lactic acid-co-glycolic acid) or lactic acid-glycolic acid copolymer; generically refer to lactic acid-glycolic acid homopolymers and copolymers, unless otherwise specified; lactic acid homopolymers are also referred to as lactic acid polymer, polylactic acids, polylactides etc., and glycolic acid homopolymers as glycolic acid polymers, polyglycolic acids, polyglycolides etc.], with preference given to poly(α-cyanoacrylic esters) etc. Greater preference is given to lactic acid-glycolic acid polymers. More preferably, lactic acid-glycolic acid polymers having a free carboxyl group at one end are used.

The biodegradable polymer may be a salt. Salts include, for example, salts with inorganic bases (e.g., alkali metals such as sodium and potassium, alkaline earth metals such as calcium and magnesium), organic bases. (e.g., organic amines such as triethylamine, basic amino acids such as arginine), and salts and complex salts with transition metals (e.g., zinc, iron, copper).

When a lactic acid-glycol acid polymer is used as a biodegradable polymer, the composition ratio (mol %) is preferably about 100/0 to about 40/60, more preferably about 100/0 to about 50/50. In the case of a long-term sustained-release microcapsule designed for zero order release of a physiological active substance over 2 months or longer, moreover, a lactic acid homopolymer having a composition ratio of 100/0 is preferably used.

The optical isomer ratio of lactic acid, one of the minimum repeat units for said "lactic acid-glycolic acid polymer" is preferably between about 75/25 and about 25/75, as of the D-configuration/L-configuration ratio (mol/mol %).

Lactic acid-glycolic acid polymers having a D-configuration/L-configuration ratio (mol/mol %) between about 60/40 and about 30/70 are commonly used.

The weight-average molecular weight of said "lactic acid-glycolic acid polymer" is normally about 3,000 to about 100,000, preferably about 3,000 to about 60,000, more preferably about 3,000 to about 50,000.

In addition, the degree of dispersion (weight-average molecular weight/number-average molecular weight) is normally about 1.2 to about 4.0, more preferably about 1.5 to 3.5.

The free carboxyl group content of said "lactic acid-glycolic acid polymer" is preferably about 20 to about 1,000 μmol (micromol), more preferably about 40 to about 1,000 μmol (micromol), per unit mass (gram) of the polymer.

Weight-average molecular weight, number-average molecular weight and degree of dispersion, as defined herein, are polystyrene-based molecular weights and degree of dispersion determined by gel permeation chromatography (GPC) with 15 polystyrenes as reference substances with weight-average molecular weights of 1,110,000, 707, 000, 455, 645, 354, 000, 189, 000, 156,055, 98,900, 66,437, 37,200, 17,100, 9,830, 5,870, 2,500, 1,303, and 504, respectively. Measurements were taken using a high-speed GPC device (produced by Toso, HLC-8120GPC, detection: Refractory Index) and a GPC column KF804Lx2 (produced by Showa Denko), with chloroform as a mobile phase. The flow rate is 1 ml/min.

The term free carboxyl group content, as used herein, is defined to be obtained by the labeling method (hereinafter referred to as "carboxyl group content as determined by the labeling method"). Specific procedures for determining this content in a polylactic acid are described below. First, W mg of the polylactic acid is dissolved in 2 ml of a 5 N hydrochloric acid/acetonitrile (v/v=4/96) mixture; 2 ml of a 0.01 M solution of o-nitrophenylhydrazine hydrochloride (ONPH) (5 N hydrochloric acid/acetonitrile/ethanol=1.02/35/15) and 2 ml of a 0.15 M solution of 1-ethyl-3-(3-dimethylaminopropyl)-carbodiimide hydrochloride (pyridine/ethanol=4v/96v) were added, followed by a reaction at 40° C. for 30 minutes, after which the solvent is removed. After water washing (4 times), the residue is dissolved in 2 ml of acetonitrile; 1 ml of a 0.5 mol/l ethanolic solution of potassium hydroxide is added, followed by a reaction at 60° C. for 30 minutes. The reaction mixture is diluted with a 1.5 N aqueous solution of sodium hydroxide to Y ml; absorbance a (/cm) at 544 nm is determined, with a 1.5 N aqueous solution of sodium hydroxide as control. Separately, with an aqueous solution of DL-lactic acid as reference, its free carboxyl group content C mol/l is determined by alkali titration. Taking the absorbance at 544 nm of the DL-lactic acid hydrazide prepared by the ONPH labeling method as B (/cm), the molar content of the free carboxyl groups per unit mass (gram) of the polymer can be calculated using the equation:

$$[COOH](mol/g)=(AYC)/(WB)$$

Although said "carboxyl group content" can also be obtained by dissolving the biodegradable polymer in a toluene-acetone-methanol mixed solvent, and titrating this solution for carboxyl groups with an alcoholic solution of potassium hydroxide, with phenolphthalein as indicator (value obtained by this method hereinafter referred to as "carboxyl group content as determined by the alkali titration method"), it is desirable that quantitation be achieved by the labeling method described above, since it is possible that the titration endpoint is made unclear as a result of competition of the hydrolytic reaction of the polyester main chain during titration.

Said "lactic acid-glycolic acid polymer" can be produced by, for example, the catalyst-free dehydration polymerization condensation method (JP-A-61-28521) from a lactic acid and a glycolic acid, or ring-opening polymerization from a lactide and a cyclic diester compound such as glycolide by means of a catalyst (*Encyclopedic Handbook of Biomaterials and Bioengineering Part A: Materials*; Volume 2, Marcel Dekker, Inc., 1995). Although the polymer obtained by the above-mentioned known method of ring-opening polymerization does not always contain a free carboxyl group at one end, it can also be used after being modified to a polymer having a given amount of carboxyl groups per unit mass, by subjecting it to the hydrolytic reaction described in EP-A-0839525.

The above-described "lactic acid-glycolic acid polymer having a free carboxyl group at one end" can be produced by a commonly known method (e.g., catalyst-free dehydration polymerization condensation, JP-A-61-28521), or by a method analogous thereto.

For instance, in making up the microcapsules for an injection, the microcapsules are dispersed in an aqueous medium together with a dispersing agent (e.g. Tween 80, HCO-60, carboxymethylcellulose, sodium alginate, etc.), a preservative (e.g. methylparaben, propylparaben, etc.), an isotonizing agent (e.g. sodium chloride, mannitol, sorbitol, glucose, etc.), or suspended in an aqueous medium together with a vegetable oil such as sesame oil or corn oil. Such dispersion or suspension is formulated into a practically usable sustained-release injection.

The aforementioned agent comprising an LHRH receptor agonist or antagonist (e.g., an LHRH receptor agonist, preferably leuprorelin or a salt thereof, more preferably leuprorelin acetate) (e.g., an agent comprising a sustained-release microcapsule comprising an LHRH receptor agonist, preferably leuprorelin or a salt thereof, more preferably leuprorelin acetate) can be administered easily as it is subcutaneously, intramuscularly, intravascularly and the like (preferably subcutaneously and the like) as an injection, an embedded agent or the like (preferably injection or the like). In addition, it can be formulated into the aforementioned various preparations and administered, and can be also used as a starting material substance to produce such preparation.

The dose of the aforementioned preparation may vary depending on the amount of LHRH receptor agonist or antagonist (e.g., LHRH receptor agonist, preferably leuprorelin or a salt thereof, more preferably leuprorelin acetate), dosage form, duration of release of LHRH receptor agonist or antagonist (e.g., LHRH receptor agonist, preferably leuprorelin or a salt thereof, more preferably leuprorelin acetate), recipient animal [e.g., warm-blooded mammal (e.g., human, mouse, rat, rabbit, sheep, swine, bovine, horse and the like)] but should be within the range of an effective dose of said LHRH receptor agonist or antagonist (e.g., LHRH receptor agonist, preferably leuprorelin or a salt thereof, more preferably leuprorelin acetate) as a pharmaceutical agent. For example, the single dose per said animal can adequately be selected within the range of about 0.01 mg to 100 mg/kg body weight, preferably about 0.02 mg to 50 mg/kg body weight, more preferably 0.05 mg to 20 mg/kg body weight.

When the aforementioned preparation is administered as an injection, generally about 0.01 to about 50 mg, preferably about 0.1 to about 20 mg, more preferably about 0.1 to about 15 mg of an LHRH receptor agonist or antagonist (e.g., LHRH receptor agonist, preferably leuprorelin or a salt thereof, more preferably leuprorelin acetate) only needs to be administered subcutaneously or intramuscularly for one dose to an adult patient (body weight 60 kg) with prostate cancer. When an injection containing a sustained-release microcapsule containing the aforementioned LHRH receptor agonist or antagonist (e.g., LHRH receptor agonist, preferably leuprorelin or a salt thereof, more preferably leuprorelin acetate) is to be administered, the dose varies depending on the duration of the drug release of the sustained-release microcapsule, wherein, for example, for administration for once in about 1 month, generally about 0.01 to about 20 mg, preferably about 0.1 to about 10 mg, more preferably about 0.1 to about 5 mg of an LHRH receptor agonist or antagonist (e.g., LHRH receptor agonist, preferably leuprorelin or a salt thereof, more preferably leuprorelin acetate) only needs to be administered subcutaneously or intramuscularly for one dose an adult patient (body weight 60 kg) with prostate cancer, and, for example, for administration for once in about 3 months, generally about 0.1 to about 30 mg, preferably about 0.1 to about 20 mg, more preferably about 0.1 to about 15 mg of an LHRH receptor agonist or antagonist (e.g., LHRH receptor agonist, preferably leuprorelin or a salt thereof, more preferably leuprorelin acetate) only needs to be administered subcutaneously or intramuscularly for one dose an adult patient (body weight 60 kg) with prostate cancer.

In the case of other animals, an amount converted based on the body weight of 60 kg can be administered.

By combining the aforementioned LHRH receptor agonist or antagonist and an androgen receptor agonist with other various combination drugs, superior effects that (1) the dose of an LHRH receptor agonist or antagonist and an androgen receptor agonist, or a combination drug can be reduced as compared to single administration thereof and side effects can be reduced, (2) the drug to be used in combination with an LHRH receptor agonist or antagonist and an androgen receptor agonist can be selected according to the condition of patients (mild symptoms, severe symptoms and the like), (3) a treatment period can be set longer by selecting a combination drug having a different action mechanism than an LHRH receptor agonist or antagonist and an androgen receptor agonist, (4) a sustained treatment effect can be designed by selecting a combination drug having a different action mechanism than an LHRH receptor agonist or antagonist and an androgen receptor agonist, (5) a synergistic effect can be obtained by a combined use of an LHRH receptor agonist or antagonist, an androgen receptor agonist and a combination drug, (6) an Add-Back therapy becomes available by a combined use of an LHRH receptor agonist or antagonist and an androgen receptor agonist and a combination drug, (7) an MAB (Maximum androgen blockade) therapy becomes available by a combined use of an LHRH receptor agonist or antagonist and an androgen receptor agonist and a combination drug, and the like can be obtained.

The Add-Back therapy means a treatment method employed when prophylaxis or treatment of a disease that exacerbates depending on sex hormone (testosterone, estrogen, estradiol and the like) in blood is desired by administering an LHRH receptor agonist to reduce these hormones, which comprises auxiliarily administering these hormone or pharmaceutical agents (e.g., SERM agents or SARM agents free of action on prostate cancer and breast cancer; hereinafter sometimes to be abbreviated as an Add-Back agent) that is considered to be equivalent to these hormones and the like, thereby to reduce these hormones, or alleviate the side effects (e.g., lower bone mass) caused by the efficacy. The Add-Back agents are mainly preferably administered by oral administration.

The MAB therapy is a treatment method to block any androgen action in the prostate gland. In other words, it refers to a surgical sterilization to block actions of androgen derived from testicular or a treatment method concurrently using an LHRH receptor agonist or antagonist and antiandrogen to block actions of an adrenogenic androgen.

For the combined use of an LHRH receptor agonist or antagonist, an androgen receptor agonist and combination drug(s), the time of administration of an LHRH receptor agonist or antagonist, an androgen receptor agonist and combination drug(s) is not limited. The LHRH receptor agonist or antagonist and the androgen receptor agonist or a preparation thereof and the combination drug(s) or a preparation thereof may be simultaneously administered to an administration object or administered in a staggered manner. The dose of the combination drug only needs to follow the dose clinically employed, and can be determined as appropriate depending on the administration object, administration route, disease, combination and the like.

The mode of administration of the pharmaceutical agent comprising the LHRH receptor agonist or antagonist and the androgen receptor agonist in combination with the combination drug (hereinafter sometimes referred to briefly as combination agent) is not particularly limited, and may be any as long as the LHRH receptor agonist or antagonist and the androgen receptor agonist and combination drug(s) are combined on administration. Such administration mode is exemplified by (1) administration of a single preparation obtained by simultaneously formulating the LHRH receptor agonist or antagonist and the androgen receptor agonist, and combination drug(s) into a preparation, (2) simultaneous administration by the same administration route of two kinds of preparations obtained by separately formulating the LHRH receptor agonist or antagonist and the androgen receptor agonist, and combination drug(s) into preparations, (3) staggered administration by the same administration route of two kinds of preparations obtained by separately formulating the LHRH receptor agonist or antagonist and the androgen receptor agonist, and combination drug(s) into preparations, (4) simultaneous administration by different administration routes of two kinds of preparations obtained by separately formulating the LHRH receptor agonist or antagonist and the androgen receptor agonist, and combination drug(s) into preparations, (5) staggered administration by different administration routes of two kinds of preparations obtained by separately formulating the LHRH receptor agonist or antagonist and the androgen receptor agonist, and combination drug(s) into preparations (e.g., administration in the order of the LHRH receptor agonist or antagonist and the androgen receptor agonist; combination drug, and administration in the reversed order) and the like.

The 1) pharmaceutical agent comprising a LHRH receptor agonist or antagonist or a salt thereof in combination with an androgen receptor agonist or a salt thereof, 2) agent for the prophylaxis or treatment of bone metastatic prostate cancer comprising an androgen receptor agonist, 3) agent for the prophylaxis or treatment of prostate cancer comprising a non-steroidal androgen receptor agonist and 4) preparation thereof comprising the aforementioned combination drug(s) in combination of the present invention have low toxicity and can be administered safely by admixing these agent with, for example, a pharmacologically acceptable carrier according to a method known per se to give a pharmaceutical composition, such as tablets (inclusive of sugar-coated tablets and film-coated tablets), powders, granules, capsules, (inclusive of soft capsules), liquids, injections, suppositories, sustained release agents and the like, for oral or parenteral (e.g., topical, rectal or intravenous administration) administration. An injection can be administered intravenously, intramuscularly, subcutaneously, into the organ or directly to the focus.

As the pharmacologically acceptable carrier usable for the production of the preparation, there are mentioned various conventional organic or inorganic carriers as a material for the preparation. Examples thereof include excipients, lubricants, binders and disintegrators for solid preparations, and solvents, solubilizing aids, suspending agents, isotonic agents, buffers and soothing agents for liquid preparations. Where necessary, conventional additives such as antiseptics, antioxidants, coloring agents, sweeteners, absorbents, moistening agent and the like can be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like.

Examples of the disintegrator include starch, carboxymethylcellulose, carboxymethylcellulose calcium, sodium carboxymethyl starch, L-hydroxypropylcellulose and the like.

Examples of the solvent include injectable water, alcohol, propylene glycol, Macrogol, sesame oil, corn oil, olive oil and the like.

Examples of the solubilizing aid include polyethylene glycol, propylene glycol, D-mannitol, benzyl benzoate, ethanol, tris-aminomethane, cholesterol, triethanolamine, sodium carbonate, sodium citrate and the like.

Examples of the suspending agent include surfactants such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonicity agent include glucose, D-sorbitol, sodium chloride, glycerine, D-mannitol and the like.

Examples of the buffer include buffers such as phosphate, acetate, carbonate, citrate and the like.

Examples of the soothing agent include benzyl alcohol and the like.

Examples of the antiseptic include p-oxybenzoates, chlorobutanol, benzyl alcohol, phenethyl alcohol, dehydroacetic acid, sorbic acid and the like.

Examples of the antioxidant include sulfite, ascorbic acid, α-tocopherol and the like.

The content of the combination drug in the preparation comprising combination drug(s) is generally about 0.01-100 wt %, preferably about 0.1-50 wt %, more preferably about 0.5-20 wt %, based on the preparation in total, though they may change depending on the preparation form.

The same contents are employed when the combination drug is formulated into the aforementioned preparations comprising a LHRH receptor agonist.

The content of the additive such as carrier in the preparation comprising the combination drug varies depending on the form of the preparation. It is generally about 1-99.99 wt %, preferably about 10-90 wt %, based on the preparation in total.

These preparations can be produced by a method known per se, which is generally employed for the preparation steps.

For example, a combination drug can be prepared into an aqueous injection together with a dispersant (e.g., Tween 80 (ATLASPOWDER USA), HCO60 (NIKKO CHEMICALS), polyethylene glycol, carboxymethylcellulose, sodium arginate, hydroxypropylmethylcellulose, dextrin etc.), a stabilizer (e.g., ascorbic acid, sodium pyrosulfite etc.), a surfactant (e.g., polysorbate 80, Macrogol etc.), a solubilizer (e.g., glycerine, ethanol etc.), a buffering agent (e.g., phosphoric acid, alkali metal salt thereof, citric acid, alkali metal salt thereof etc.), an isotonicity agent (e.g., sodium chloride, potassium chloride, mannitol, sorbitol, glucose etc.), a pH adjusting agent (hydrochloric acid, sodium hydroxide etc.), a preservative (ethyl p-hydroxybenzoate, benzoic acid, methylparaben, propylparaben, benzyl alcohol etc.), a solubilizer (e.g., conc. glycerine, meglumine etc.), a solubilizing aid (e.g., propylene glycol, sucrose etc.), a soothing agent (e.g., glucose, benzyl alcohol etc.) and the like, or into an oil-based injection by dissolving, suspending or emulsifying in a vegetable oil (e.g., olive oil, sesame oil, cottonseed oil, corn oil etc.) or a solubilizing aid such as propylene glycol etc., and used as an injection.

An oral formulation can be produced by a method known per se by admixing a combination drug with an excipient (e.g., lactose, sucrose, starch and the like), a disintegrant (e.g., starch, calcium carbonate and the like), a binder (e.g., starch, gum arabic, carboxymethyl cellulose, polyvinyl pyrrolidone, hydroxypropyl cellulose and the like) or a lubricant (e.g., talc, magnesium stearate, polyethylene glycol 6000 and the like) and compressing the mixture, optionally followed by a coating process known per se for the purpose of masking a taste, forming an enteric coat, or achieving a sustained release. Such coating may, for example, be hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (ROHME, Germany, a copolymer of methacrylic acid and acrylic acid), a dye (e.g., colcothar, titanium oxide etc.) and the like. The preparation for oral administration may be either a rapid release preparation or a sustained release preparation.

A suppository can be produced by making a combination drug into an oily or aqueous solid, semisolid or liquid composition. Examples of the oily base to be used for such a composition include glyceride of higher fatty acid (e.g., cacao butter, Witepsol (Dynamit Nobel, Germany etc.), medium fatty acid (e.g., miglyol (Dynamit Nobel, Germany etc.), vegetable oil (e.g., sesame oil, soybean oil, cottonseed oil etc.) and the like. Examples of the aqueous base include polyethylene glycols, propylene glycol and the like. Examples of the aqueous gel base include natural gums, cellulose derivative, vinyl polymer, acrylate polymer and the like.

Examples of the above-mentioned sustained release preparation include sustained release microcapsule and the like.

A sustained release microcapsule can be prepared by a method known per se. For example, a sustained release preparation shown in the following [2] is preferably formed and administered.

In the following, [1] an injection of a combination drug and preparation thereof, [2] a sustained release preparation or a rapid release preparation of a combination drug and preparation thereof, and [3] a sublingual tablet, buccal or oral cavity rapid disintegrator of a combination drug and preparation thereof are concretely explained.

[1] Injection and Preparation Thereof

An injection containing a combination drug dissolved in water is preferable. The injection may contain benzoate and/or salicylate.

The injection is obtained by dissolving both a combination drug and, where desired, benzoate and/or salicylate in water.

The salt of the above-mentioned benzoic acid and salicylic acid includes, for example, alkali metal salts such as sodium, potassium and the like, alkaline earth metal salts such as calcium, magnesium and the like, ammonium salt, meglumine salt, and organic acid salt such as trometamol and the like, and the like.

The concentration of a combination drug in the injection is about 0.5-50 w/v %, preferably about 3-20 w/v %. The concentration of the benzoate and/or salicylate is preferably 0.5-50 w/v %, more preferably 3-20 w/v %.

This agent may contain additives generally used for injections, such as a stabilizer (e.g., ascorbic acid, sodium pyrosulfite etc.), a surfactant (e.g., polysorbate 80, Macrogol etc.), a solubilizer (e.g., glycerine, ethanol etc.), a buffering agent (e.g., phosphoric acid, alkali metal salt thereof, citric acid, alkali metal salt thereof etc.), an isotonicity agent (e.g., sodium chloride, potassium chloride etc.), a dispersing agent (e.g., hydroxypropylmethylcellulose, dextrin), a pH adjusting agent (hydrochloric acid, sodium hydroxide etc.), a preservative (ethyl p-hydroxybenzoate, benzoic acid etc.), a solubilizer (e.g., conc. glycerine, meglumine etc.), a solubilizing aid (e.g., propylene glycol, sucrose etc.), a soothing agent (e.g., glucose, benzyl alcohol etc.) and the like as appropriate. These additives are added in a proportion generally employed for injections.

The injection is preferably adjusted to pH 2-12, preferably 2.5-8.0, by the use of a pH adjusting agent.

The injection can be obtained by dissolving both LHRH receptor agonist or a combination drug and, where desired, benzoate and/or salicylate, and where necessary, the above-mentioned additives in water. These may be dissolved in any order in a suitable manner as in conventional production of injections.

The injectable aqueous solution is preferably heated and, in the same manner as with conventional injections, subjected to, for example, sterilization by filtration, high pressure sterilization by heating and the like to provide an injection.

The injectable aqueous solution is preferably subjected to high pressure sterilization by heating at, for example, 100° C.-121° C. for 5 min-30 min.

It may be prepared into an antibacterial solution, so that it can be used as a preparation for plural subdivided administrations.

[2] Sustained Release Preparation or Rapid Release Preparation and Preparation Thereof A sustained release preparation wherein a core containing a combination drug is covered on demand with a film forming agent, such as a water-insoluble material, a swellable polymer and the like, is preferable. For example, a sustained release preparation for oral administration once a day is preferable.

The water-insoluble material to be used for the film forming agent is, for example, cellulose ethers such as ethylcellulose, butylcellulose and the like; cellulose esters such as cellulose acetate, cellulose propionate and the like; polyvinyl esters such as poly(vinyl acetate), poly(vinyl butyrate) and the like; acrylic polymers such as acrylic acid/methacrylic acid copolymer, methyl methacrylate copolymer, ethoxyethyl methacrylate/cinnamoethyl methacrylate/aminoalkyl methacrylate copolymer, polyacrylic acid, polymethacrylic acid, methacrylic acid alkylamide copolymer, poly(methyl methacrylate), polymethacrylate, polymethacryl amide, aminoalkyl methacrylate copolymer, poly(methacrylic anhydride) and glycidyl methacrylate copolymer, particularly Eudragits (Rohm Pharma) such as Eudragit RS-100, RL-100, RS-30D, RL-30D, RL-PO, RS-PO (ethyl acrylate-methyl methacrylate-trimethyl chloride methacrylate-ammonium ethyl copolymer), Eudragit NE-30D (methyl methacrylate-ethyl acrylate copolymer) and the like, and the like; hydrogenated oils such as hydrogenated castor oil (e.g., Lubri wax (Freund Inc.) and the like) and the like; waxes such as carnauba wax, fatty acid glycerine ester, paraffin and the like; polyglycerine fatty acid ester and the like.

As the swellable polymer, a polymer having an acidic dissociable group, which shows pH-dependent swelling, is preferable, and a polymer having an acidic dissociable group, which shows less swelling in an acidic range, such as in the stomach, but otherwise in a neutral range, such as in the small intestine and large intestine, is preferable.

Examples of the polymer having an acidic dissociable group, which shows pH-dependent swelling, include crosslinking type polyacrylic acid polymers such as Carbomer 934P, 940, 941, 974P, 980, 1342 and the like, polycarbophil, calcium polycarbophil (all mentioned above are the product of BF Goodrich), HI-BIS-WAKO 103, 104, 105, 304 (all being products of Waco Pure Chemicals Industries, Ltd.) and the like.

The film forming agent to be used for the sustained release preparation may further contain a hydrophilic material.

Examples of the hydrophilic material include polysaccharides optionally having a sulfuric acid group such as pullulan, dextrin, alkali metal salt of alginic acid and the like; polysaccharides having a hydroxy alkyl group or a carboxy alkyl group such as hydroxypropylcellulose, hydroxypropylmethylcellulose, sodium carboxymethylcellulose and the like; methylcellulose, polyvinylpyrrolidone, polyvinyl alcohol, polyethylene glycol and the like.

The content of the water-insoluble material of the film forming agent for a sustained release preparation is about 30-about 90% (w/w), preferably about 35-about 80% (w/w), more preferably about 40-75% (w/w), and the content of the swellable polymer is about 3-about 30% (w/w), preferably about 3-about 15% (w/w). The film forming agent may further contain a hydrophilic material, in which case the content of the hydrophilic material for film forming agent is not more than about 50% (w/w), preferably about 5-about 40% (w/w), more preferably about 5-about 35% (w/w). As used herein, the above-mentioned % (w/w) is a percentage relative to the film forming agent composition wherein the solvent (e.g., water, lower alcohol such as methanol, ethanol and the like) has been removed from the film forming liquid agent.

A sustained release preparation is produced by preparing a core containing a drug as exemplarily mentioned below, and coating the resulting core with a film forming liquid agent prepared by dissolving by heating or dissolving or dispersing in a solvent a water-insoluble material, a swellable polymer and the like.

I. Preparation of Core Containing a Drug

The form of the core containing a drug (hereinafter sometimes simply referred to as a core) to be coated with a film forming agent is not particularly limited, but it is preferably formed into particles such as granules, fine granules and the like.

When the core is made of granules or fine granules, the average particle size thereof is preferably about 150-2,000 µm, more preferably about 500-about 1,400 µm.

The core can be prepared by a typical production method. For example, a drug is mixed with suitable excipients, binders, disintegrators, lubricants, stabilizers and the like, and subjected to wet extrusion granulation, fluidized bed granulation and the like.

The drug content of the core is about 0.5-about 95% (w/w), preferably about 5.0-about 80% (w/w), more preferably about 30-about 70% (w/w).

Examples of the excipient to be contained in the core include saccharides such as sucrose, lactose, mannitol, glucose and the like, starch, crystalline cellulose, calcium phosphate, cornstarch and the like. Of these, crystalline cellulose and corn starch are preferable.

Examples of the binder include polyvinyl alcohol, hydroxypropylcellulose, polyethylene glycol, polyvinylpyrrolidone, Pluronic F68, gum arabic, gelatin, starch and the like. Examples of the disintegrator include carboxymethylcellulose calcium (ECG505), crosscarmellose sodium (Ac-Di-Sol), crosslinked polyvinylpyrrolidone (Crospovidone), low substituted hydroxypropylcellulose (L-HPC) and the like. Of these, hydroxypropylcellulose, polyvinylpyrrolidone and low substituted hydroxypropylcellulose are preferable. Examples of the lubricant and coagulation preventive include talc, magnesium stearate and inorganic salts thereof, and examples of the lubricant include polyethylene glycol and the like. Examples of the stabilizer include acids such as tartaric acid, citric acid, succinic acid, fumaric acid, maleic acid and the like.

The core can be also prepared by, besides the above-mentioned production methods, for example, rolling granulation wherein a drug or a mixture of a drug and an excipient, a lubricant and the like is added by small portions while spraying a binder dissolved in a suitable solvent such as water, lower alcohol (e.g., methanol, ethanol and the like) and the like on an inert carrier particles to be the center of the core, a pan coating method, a fluidized bed coating method or a melt granulating method. Examples of the inert carrier particle include those prepared from sucrose, lactose, starch, crystalline cellulose and waxes, which preferably have an average particle size of about 100 µm-about 1,500 µm.

To separate the drug contained in the core from the film forming agent, the surface of the core may be coated with a protective agent. Examples of the protective agent include the aforementioned hydrophilic material, water-insoluble material and the like. As the protective agent, preferably polyethylene glycol, polysaccharides having a hydroxy alkyl group or a carboxy alkyl group, more preferably hydroxypropylmethylcellulose and hydroxypropylcellulose are used. The protective agent may contain, as a stabilizer, an acid such as tartaric acid, citric acid, succinic acid, fumaric acid, maleic acid and the like, and a lubricant such as talc and the like. When the protective agent is used, the amount to be coated is about 1-about 15% (w/w), preferably about 1-about 10% (w/w), more preferably about 2-about 8% (w/w), relative to the core.

The protective agent can be coated by a typical coating method. Specifically, the protective agent is, for example, spray-coated to the core by a fluidized bed coating method, a pan coating method, and the like.

II. Coating of Core with a Film Forming Agent

The core obtained in the aforementioned I is coated with a film forming liquid agent prepared by dissolving by heating or dissolving or dispersing in a solvent the aforementioned water-insoluble material, a pH-dependent swellable polymer, and a hydrophilic material to provide a sustained release preparation.

For coating a core with a film forming liquid agent, for example, a spray coating method and the like can be employed.

The composition ratio of the water-insoluble material, swellable polymer or hydrophilic material in the film forming liquid agent is suitably determined such that each component of the coating film meets the aforementioned content.

The coating amount of the film forming agent is about 1-about 90% (w/w), preferably about 5-about 50% (w/w), more preferably about 5-35% (w/w), relative to the core (exclusive of the coating amount of protective agent).

As the solvent for the film forming liquid agent, water or organic solvents can be used alone or in a mixture of the both. The mixing ratio (water/organic solvent:weight ratio) of water and the organic solvent in the mixture can vary within the range of 1-100%, which is preferably 1-about 30%. The organic solvent is not subject to any particular limitation as long as it dissolves the water-insoluble material. For example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Of these, lower alcohol is preferable, and ethyl alcohol and isopropyl alcohol are particularly preferable. Water and a mixture of water and an organic solvent are preferably used as a solvent of the film forming agent. Where necessary, the film forming liquid agent may contain an acid such as tartaric acid, citric acid, succinic acid, fumaric acid, maleic acid and the like for the stabilization of the film forming liquid agent.

When spray coating is employed, the method follows a conventional coating method, which specifically includes spray coating the core with a film forming liquid agent by, for example, a fluidized bed coating method, a pan coating method and the like. Where necessary, talc, titanium oxide, magnesium stearate, calcium stearate, light anhydrous silicic acid and the like may be added as a lubricants and glycerine fatty acid ester, hydrogenated castor oil, triethyl citrate, cetyl alcohol, stearyl alcohol and the like may be added as a plasticizer.

After coating with a film forming agent, an antistatic agent such as talc and the like may be added as necessary.

A rapid release preparation may be a liquid (solution, suspension, emulsion and the like) or a solid (particle, pill, tablet and the like). An agent for oral administration, and an agent for parenteral administration, such as injection and the like, are used, with preference given to an agent for oral administration.

A rapid release preparation may generally contain, in addition to the drug, which is an active ingredient, carriers, additives and excipients (hereinafter sometimes simply referred to as excipient) conventionally used in the field of preparation. The excipient for a preparation is not subject to any particular limitation as long as it is conventionally employed as an excipient for a preparation. For example, the excipient for the oral solid preparation includes lactose, starch, corn starch, crystalline cellulose (Asahi Kasei Corporation, Avicel PH101 and the like), powder sugar, granulated sugar, mannitol, light anhydrous silicic acid, magnesium carbonate, calcium carbonate, L-cysteine and the like, preferably corn starch and mannitol and the like. These excipients may be used alone or in combination. The content of the excipient is, for example, about 4.5-about 99.4 w/w %, preferably about 20-about 98.5 w/w %, more preferably about 30-about 97 w/w %, of the total amount of the rapid release preparation.

The drug content of the rapid release preparation is appropriately determined from the range of about 0.5-about 95%, preferably about 1-about 60%, of the total amount of the rapid release preparation.

When the rapid release preparation is an oral solid preparation, it generally contains a disintegrator in addition to the above-mentioned components. Examples of the disintegrator include calcium carboxymethylcellulose (Gotoku Pharmaceutical Co., Ltd., ECG-505), crosscarmellose sodium (e.g., Asahi Kasei Corporation, acjizol), Crospovidone (e.g., colidone CL, BASF), low substituted hydroxypropylcellulose (Shin-Etsu Chemical Co., Ltd.), carboxymethyl starch (Matsutani Chemical Industry Co., Ltd.), sodium carboxymethyl starch (Kimura Sangyo, exprotab), partially a starch (PCS, Asahi Kasei Corporation) and the like. For example, one capable of disintegrating granules by water absorption, swelling, forming a channel between the active ingredient constituting the core and an excipient upon contact with water and the like can be used. These disintegrators can be used alone or in combination. The amount of the disintegrator is appropriately determined depending on the kind of the combination drug to be used and amount thereof, design of the release preparation and the like. It is generally about 0.05-about 30 w/w %, preferably about 0.5-about 15 w/w %, relative to the total amount of the rapid release preparation.

When the rapid release preparation is an oral preparation, the oral solid preparation may further contain, in addition to the above-mentioned composition, typical additives used for solid preparation on demand. Examples of the additive include a binder (e.g., sucrose, gelatin, gum arabic powder, methylcellulose, hydroxypropylcellulose, hydroxypropylmethylcellulose, carboxymethylcellulose, polyvinylpyrrolidone, Pullulan, dextrin etc.), a lubricant (e.g., polyethylene glycol, magnesium stearate, talc, light anhydrous silicic acid (e.g., Aerosil (Nippon Aerosil)), a surfactant (e.g., anionic surfactant such as sodium alkylsulfate etc., non-ionic surfactant such as polyoxyethylene fatty acid ester and polyoxyethylenesorbitan fatty acid ester, polyoxyethylene castor oil derivative etc., and the like), a coloring agent (e.g., tar color, caramel, iron oxide red, titanium oxide, riboflavins), where necessary, a corrigent (e.g., a sweetener, flavor etc.), an absorbent, an antiseptic, a moistening agent, an antistatic agent and the like. As the stabilizer, an organic acid such as tartaric acid, citric acid, succinic acid, fumaric acid and the like may be added.

Examples of the above-mentioned binder preferably include hydroxypropylcellulose, polyethylene glycol, polyvinylpyrrolidone and the like.

The rapid release preparation can be prepared based on the conventional preparation method, by mixing each of the aforementioned components, and where necessary, further kneading and forming. The above-mentioned mixing can be performed by a conventional method, such as mixing, kneading and the like. Specifically, for example, when a rapid release preparation is formed into particles, a vertical granulator, a universal kneader (HATA Tekkohjo), a fluidized bed granulator FD-5S (Powrex Corporation) and the like are used for mixing, which is followed by granulating by wet extrusion granulation, fluidized bed granulation and the like, to give the preparation, as in the preparation of the core of the aforementioned sustained release preparation.

The rapid release preparation and the sustained release preparation thus obtained may be used as they are. Alternatively, after suitable separate preparation along with an excipient for a preparation and the like according to a conventional method, they may be administered simultaneously or at optional administration intervals. Alternatively, they may be each prepared into a single preparation for oral administration (e.g., granule, fine granule, tablet, capsule and the like) as they are or together with excipient for preparation and the like as appropriate. The both preparations are converted to granules or fine granules and filled in a single capsule and the like to give a preparation for oral administration.

[3] A Sublingual Tablet, Buccal or Oral Cavity Rapid Disintegrator and Preparation Thereof The sublingual tablet, buccal preparation and oral cavity rapid disintegrator may be a solid preparation such as tablet and the like or an oral cavity mucous membrane adhesion tablet (film).

As the sublingual tablet, buccal or oral cavity rapid disintegrator, a preparation containing a combination drug and an excipient is preferable. It may contain auxiliaries such as a lubricant, an isotonic agent, a hydrophilic carrier, a water dispersible polymer, a stabilizer and the like. For easy absorption and enhanced bioavailability, β-cyclodextrin or β-cyclodextrin derivative (e.g., hydroxypropyl-β-cyclodextrin and the like) and the like may be contained.

Examples of the above-mentioned excipient include lactose, sucrose, D-mannitol, starch, crystalline cellulose, light anhydrous silicic acid and the like. Examples of the lubricant include magnesium stearate, calcium stearate, talc, colloidal silica and the like, particularly magnesium stearate and colloidal silica are preferable. Examples of the isotonicity agent include sodium chloride, glucose, fructose, mannitol, sorbitol, lactose, saccharose, glycerine, urea and the like, particularly mannitol is preferable. Examples of the hydrophilic carrier include swellable hydrophilic carriers such as crystalline cellulose, ethylcellulose, crosslinked polyvinylpyrrolidone, light anhydrous silicic acid, silicic acid, dicalcium phosphate, calcium carbonate and the like, particularly crystalline cellulose (e.g., microcrystalline cellulose and the like) is preferable. Examples of the water dispersible polymer include gum (e.g., gum tragacanth, acacia gum, guar gum), alginate (e.g., sodium alginate), cellulose derivative (e.g., methylcellulose, carboxymethylcellulose, hydroxymethylcellulose, hydroxypropylcellulose, hydroxypropylmethylcellulose), gelatin, soluble starch, polyacrylic acid (e.g., carbomer), polymethacrylic acid, polyvinyl alcohol, polyethylene glycol, polyvinylpyrrolidone, polycarbofil, ascorbic palmitate and the like, with preference given to hydroxypropylmethylcellulose, polyacrylic acid, alginate, gelatin, carboxymethylcellulose, polyvinylpyrrolidone, polyethylene glycol and the like. Particularly, hydroxypropylmethylcellulose is preferable. Examples of the stabilizer include cysteine, thiosorbitol, tartaric acid, citric acid, sodium carbonate, ascorbic acid, glycine, sodium sulfite and the like, particularly, citric acid and ascorbic acid are preferable.

The sublingual tablet, buccal and oral cavity rapid disintegrator can be produced by mixing a combination drug and an excipient by a method know per se. Where desired, the above-mentioned auxiliaries such as a lubricant, an isotonic agent, a hydrophilic carrier, a water dispersible polymer, a stabilizer, a coloring agent, a sweetener, an antiseptic and the like may be contained. After mixing the above-mentioned components simultaneously or with time staggering, the mixture is compression formed under pressure to give sublingual tablet, buccal or oral cavity rapid disintegrator. To achieve a suitable hardness, a solvent such as water, alcohol and the like is used to moisten or wet as necessary before and after the compression forming. After the forming, the tablets may be dried.

When a mucous membrane adhesion tablet (film) is produced, a combination drug and the above-mentioned water dispersible polymer (preferably, hydroxypropylcellulose, hydroxypropylmethylcellulose), an excipient and the like are dissolved in a solvent such as water and the like, and the obtained solution is cast to give a film. In addition, an additive such as a plasticizer, a stabilizer, an antioxidant, a preservative, a coloring agent, a buffer, a sweetener and the like may be added. To impart suitable elasticity to the film, glycols such as polyethylene glycol, propylene glycol and the like may be added, and to increase adhesion of the film to the oral cavity mucous membrane lining, bioadhesive polymer (e.g., polycarbofil, carbopol) may be added. The casting includes pouring the solution on a non-adhesive surface, spreading the solution in a uniform thickness (preferably about 10-1000µ) with a coating tool such as doctor blade and the like and drying the solution to give a film. The film thus formed may be dried at room temperature or under heating and cut into a desired surface area.

Examples of preferable oral cavity rapid disintegrator are a solid rapid diffusing administration agent having a net structure of a combination drug and water soluble or water diffusable carrier which are inert to a combination drug. The net structure can be obtained by sublimation of a solvent from the solid composition consisting of a solution obtained by dissolving a combination drug in a suitable solvent.

The oral cavity rapid disintegrator preferably contains, in addition to a combination drug, a matrix forming agent and a secondary component.

Examples of the matrix forming agent include animal proteins or vegetable proteins such as gelatins, dextrins, soybeans, wheat, psyllium seed protein and the like; rubber substances such as gum arabic, guar gum, agar, xanthan and the like; polysaccharides; alginic acids; carboxymethylcelluloses; carrageenans; dextrans; pectins; synthetic polymers such as polyvinylpyrrolidone and the like; a material derived from a gelatin-gum arabic complex and the like. In addition, saccharides such as mannitol, dextrose, lactose, galactose, trehalose and the like; cyclic saccharides such as cyclodextrin and the like; inorganic salts such as sodium phosphate, sodium chloride, aluminum silicate and the like; amino acid having 2 to 12 carbon atoms such as glycine, L-alanine, L-aspartic acid, L-glutamine acid, L-hydroxyproline, L-isoleucine, L-leucine, L-phenylalanine and the like are exemplified.

It is possible to introduce one or more matrix forming agents into a solution or suspension before preparation into a solid. Such matrix forming agent may exist with a surfactant or without a surfactant. The matrix forming agent can form a matrix, and also can help maintain the diffusion of a combination drug in the solution or suspension.

The composition may contain a secondary component such as a preservative, an antioxidant, a surfactant, a thickener, a coloring agent, a pH adjusting agent, a flavor, a sweetener, a taste masking reagent and the like. Examples of a suitable coloring agent include red, black and yellow ferric oxides and FD&C dyes of Ellis & Everard, such as FD&C blue NO. 2, FD&C red No. 40 and the like. A suitable flavor contains mint, raspberry, licorice, orange, lemon, grapefruit, caramel, vanilla, cherry, grape flavor and a combination of these. Suitable pH adjusting agent includes citric acid, tartaric acid, phosphoric acid, hydrochloric acid and maleic acid. Suitable sweetener includes aspartame, acesulfame K, thaumatin and the like. Suitable taste masking agent includes sodium bicarbonate, ion exchange resin, cyclodextrin inclusion compound, adsorbent substance and microcapsuled apomorphine.

As the preparation, one containing a combination drug generally in a proportion of about 0.1-about 50 wt %, preferably about 0.1-about 30 wt %, which is capable of dissolving 90% or more of a combination drug in water for about 1 min-about 60 min, preferably about 1 min-about 15 min, more preferably about 2 min-about 5 min, such as the above-mentioned sublingual tablet, buccal and the like, and an oral cavity rapid disintegrator that disintegrates within 1-60 sec, preferably 1-30 sec, more preferably 1-10 sec, after being placed in an oral cavity, are preferable.

The content of the above-mentioned excipient in the whole preparation is about 10-about 99 wt %, preferably about 30-about 90 wt %. The content of the β-cyclodextrin or β-cyclodextrin derivative relative to the whole preparation is 0-about 30 wt %. The content of the lubricant relative to the whole preparation is about 0.01-about 10 wt %, preferably about 1-about 5 wt %. The content of the isotonicity agent relative to the whole preparation is about 0.1-about 90 wt %, preferably about 10-about 70 wt %. The content of the hydrophilic carrier relative to the whole preparation is about 0.1-about 50 wt %, preferably about 10-about 30 wt %. The content of the water dispersible polymer relative to the whole preparation is about 0.1-about 30 wt %, preferably about 10-about 25 wt %. The content of the stabilizer relative to the whole preparation is about 0.1-about 10 wt %, preferably about 1-about 5 wt %. The above-mentioned preparation may contain additives such as a coloring agent, a sweetener, an antiseptic and the like as necessary.

While the dose of the preparation comprising a combination drug varies depending on the kind of the combination drug, the patient's age, body weight and condition, the dosage form, the mode and the period of the treatment, the respective amounts of the combination drug may be, for example, about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg per day, for a patient (adult weighing about 60 kg) with, for example, prostate cancer, said daily dose being given intravenously once or in several portions during a day. It is a matter of course that a lower daily dose may be sufficient or an excessive dose may be required since the dose may vary depending on various factors as discussed above.

The combination drug may be contained in any amount as long as a side effect does not pose a problem. While the daily dose of the combination drug may vary depending on the disease state, age, sex, body weight and difference in sensitivity of the administration object, timing and interval of administration, characteristics, dispensing and kind of the pharmaceutical preparation, the kind of the active ingredient and the like, and is not particularly limited, the amount of the drug is generally about 0.001-2000 mg, preferably about 0.01-500 mg, more preferably about 0.1-100 mg, per 1 kg body weight of mammal by oral administration, which is generally administered once or in 2 to 4 portions during a day.

When the preparation comprising a combination drug is administered, it may be administered at the same time. However, a combination drug may be administered first, and then the LHRH receptor agonist or antagonist and an androgen receptor agonist may be administered. Alternatively, the LHRH receptor agonist or antagonist and an androgen receptor agonist may be administered first, and then a combination drug may be administered. For time-staggered administration, the time difference varies depending on the active ingredient to be administered, dosage form and administration route. For example, when the combination drug is to be administered first, the LHRH receptor agonist or antagonist and an androgen receptor agonist are administered within 1 min-3 days, preferably 10 min-1 day, more preferably 15 min-1 hour, after the administration of the combination drug. When the LHRH receptor agonist or antagonist and an androgen receptor agonist are to be administered first, the combination drug is administered within 1 min-1 day, preferably 10 min-6 hrs., more preferably 15 min-1 hour, after the administration of the LHRH receptor agonist or antagonist and an androgen receptor agonist.

Abbreviations for amino acids of polypeptide, peptides, protective groups and the like used in the present specification are based on abbreviations specified by the IUPAC-IUB Commission on Biochemical Nomenclature or abbreviations in common use in relevant fields. When there is a possibility of the presence of an optical isomer in amino acid, the L-configuration is used, unless otherwise stated.

Examples of the abbreviations are shown in the following.
Abu: aminobutyric acid
Aibu: 2-aminobutyric acid
Ala: alanine
Arg: arginine
Gly: glycine
His: histidine
Ile: isoleucine
Leu: leucine
Met: methionine
Nle: norleucine
Nval: norvaline
Phe: phenylalanine
Phg: phenylglycine
Pro: proline
(Pyr)Glu: pyroglutamic acid
Ser: serine
Thr: threonine
Trp: tryptophan
Tyr: tyrosine
Val: valine
D2Nal: D-3-(2-naphthyl)alanine residue
DSer(tBu): O-tert-butyl-D-serine
DHis(ImBzl): $N^{im}$-benzyl-D-histidine
PAM: phenylacetamidemethyl
Boc: t-butyloxycarbonyl
Fmoc: 9-fluorenylmethyloxycarbonyl
Cl—Z: 2-chloro-benzyloxycarbonyl
Br—Z: 2-bromo-benzyloxycarbonyl
Bzl: benzyl
$Cl_2$-Bzl: 2,6-dichlorobenzyl
Tos: p-toluenesulfonyl
HONb: N-hydroxy-5-norbornen-2,3-dicarboxylmide
HOBt: 1-hydroxybenzotriazole
HOOBt: 3-hydroxy-3,4-dihydro-4-oxo-1,2,3-benzotriazine
MeBzl: 4-methylbenzyl
Bom: benzyloxymethyl
Bum: t-butoxymethyl
Trt: trityl
DNP: dinitrophenyl
DCC: N,N'-dicyclohexylcarbodiimide

EXAMPLES

The present invention is explained in more detail in the following by referring to Reference Examples and Examples.

Reference Example 1

Leuprorelin Acetate-Containing Microcapsule

Leuprorelin acetate (5.8 g) was dissolved in 6.7 ml of distilled water. Thereto was added dichloromethane solution (138 g) containing polylactic acid (weight average molecular weight: 15000) (51.6 g) separately dissolved and filtered, and emulsified with stirring (rotation: about 6000 rpm) in an autominimixer for 9 min. and adjusted to 15° C. This was added to 0.1% aqueous polyvinyl alcohol (PVA) solution (13.5 L) dissolved, filtered and adjusted to the same temperature in advance and emulsified. In this case, HOMOMIC LINE FLOW (TOKUSHU KIKA KOGYO CO., LTD.) was used and the mixture was emulsified at a rotation number of the mixer of about 7000 rpm. This W/O/W emulsion was desolvented with gently stirring for about 3 hrs. (an in-water drying method).

The obtained microcapsules were passed through a 74 μm sieve to remove coarse particles, separated by filtration or centrifugal separation. This was washed with distilled water, and after removing a free drug and PVA and redispersed in a small amount of water. D mannitol (8.7 g) was dissolved and the mixture was passed through a sieve and lyophilized. The shelf temperature during drying was gradually raised and finally dried at 52° C. for 69 hrs. This was pulverized by passing through a sieve to give a microcapsule powder. This operation gave 58 g of 15% D-mannitol-containing microcapsule powder.

Reference Example 2

Raloxifene-Containing Injection

| (1) | raloxifene | 5.0 mg |
|---|---|---|
| (2) | sodium chloride | 20.0 mg |
| (3) | distilled water | to make total amount 2 ml |

Testosterone (5.0 mg) and sodium chloride (20.0 mg) are dissolved in distilled water and water is added to make the total amount 2.0 ml. The solution is filtered and filled in a 2 ml ampoule under sterile conditions. The ampoule is sterilized and sealed to give a solution for injection.

Reference Example 3

Tablet Containing Testosterone

| (1) | Testosterone | 50 mg |
|---|---|---|
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Carboxymethylcellulose calcium | 20 mg |
| | total | 120 mg |

According to a conventional method, the aforementioned (1)-(6) were mixed and tableted by a tableting machine to give tablets.

Reference Example 4

Establishment of Highly Androgen Receptor Agonist Sensitive Cell Line (LNCaP-hr and MDA PCa2b-hr Cell Line)

LNCaP-FGC and MDA PCa 2b cell lines were cultured in a culture medium free of androgen (RPMI1640+10% Dextran Charcoal (DCC)-Fetal Bovine Serum (FBS) for LNCaP-FGC and Ham's F-12K+25 ng/ml cholera toxin+10 ng/ml EGF+0.005 mM phosphoethanolamine+100 pg/ml hydrocortisone+45 nM selenious acid+0.005 mg/ml insulin+20% DCC-FBS for MDA PCa 2b). The lines did not grow at first but started to grow after continued culture for 3 to 8 months or longer. The cells thereof were named LNCaP-hr and MDA PCa 2b-hr, respectively.

Example 1

Effect on Cell Growth in the Presence of Androgen (Method) LNCaP-hr (cultured for 60 weeks in culture broth free of androgen) and LNCaP-FGC cells were plated on a 24 well plate at 40000 cells/mL/well, 0.01 to 10 ng/mL of testosterone was added the next day, and the cells were counted 3 days after the addition. In addition, MDA PCa 2b-hr (cultured for 61 weeks in culture broth free of androgen) and MDA PCa 2b cells were plated on a 24 well plate at 40000 cells/mL/well, 0.1 to 100 ng/mL of testosterone was added the next day, and the cells were counted 4 days after the addition.

Figure 2:
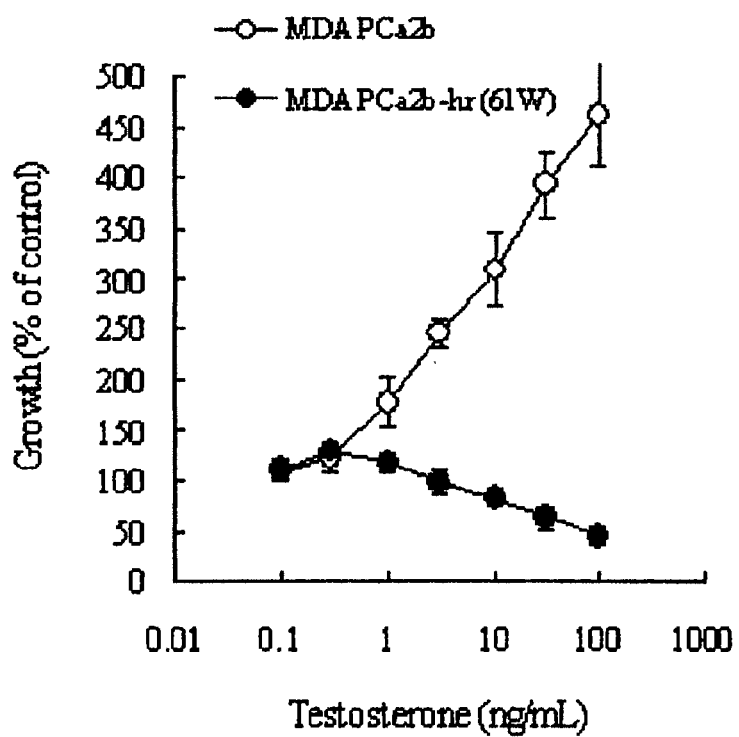
FIG. 2 shows cell growth rates of MDA PCa 2b and MDA PCa 2b-hr (highly androgen sensitive cell lines) cultured in the presence of testosterone, wherein the transverse axis shows testosterone concentration and the vertical axis shows cell growth rates.

(Results) The growth of LNCaP-FGC and MDA PCa 2b was promoted by testosterone [FIGS. 1 and 2]. In contrast, the growth of LNCaP-hr and MDA PCa 2b-hr cells were suppressed by testosterone [FIGS. 1 and 2].

Example 2

The preparation obtained in Reference Example 1 is combined with the preparation obtained in Reference Example 2.

Example 3

The preparation obtained in Reference Example 1 is combined with the preparation obtained in Reference Example 3.

INDUSTRIAL APPLICABILITY

By combining an LHRH receptor agonist or antagonist with an androgen receptor agonist, superior effects such as improved prophylactic or therapeutic effect on various diseases, reduction of side effects and the like can be achieved.

The invention claimed is:

1. A method for treating prostate cancer, which comprises administering an effective amount of an LHRH receptor agonist or antagonist or a salt thereof to a mammal in need thereof, and after a prostate cancer cell has become highly sensitive to androgen, administering an effective amount of an androgen receptor agonist or a salt thereof, wherein the LHRH receptor agonist is a peptide of the formula:

(Pyr)Glu-R$^1$-Trp-Ser-R$^2$-R$^3$-R$^4$-Arg-Pro-R$^5$     (I)

wherein R$^1$ is His, Tyr, Trp or p-NH$_2$-Phe; R$^2$ is Tyr or Phe; R$^3$ is Gly or a D type amino acid residue optionally having substituent(s); R$^4$ is Leu, Ile or Nle; and R$^5$ is Gly-NH—R$^6$, wherein R$^6$ is a hydrogen atom or an alkyl group optionally having a hydroxyl group, NH—R$^7$, wherein R$^7$ is a hydrogen atom, an amino group, an alkyl group optionally having a hydroxyl group, or —NH—CO—NH$_2$; wherein the D type amino acid residue for R$^3$ is a-D-amino acid having up to 9 carbon atoms, which is selected from the group consisting of D-Leu, Ile, Nle, Val, Nval, Abu, Phe, Phg, Ser, Thr, Met, Ala, Trp, and a-Aibu; the substituent for R$^3$ is selected from the group consisting of tert-butyl, tert-butoxy, tert-butoxycarbonyl, methyl, dimethyl, trimethyl, 2-naphthyl, indolyl-3-yl, 2-methylindolyl, and benzyl-imidazo-2-yl; and the alkyl group for R$^6$ or R$^7$ is a C$_{1-4}$ alkyl group selected from the group consisting of methyl, ethyl, propyl, isopropyl, butyl, isobutyl, sec-butyl and tert-butyl or a salt thereof;

the LHRH receptor antagonist is selected from the group consisting of abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione, and 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione hydrochloride; and the androgen receptor agonist is a steroidal androgen receptor agonist selected from the group consisting of dehydroepiandrosterone, testosterone, dihydrotestosterone, androstenedione, Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylestrenol and Norbolethone, or a salt thereof.

2. A method for treating prostate cancer, which comprises 1) administering an androgen receptor agonist or a salt thereof to a highly androgen sensitive prostate cancer cell for a certain time period, 2) thereafter when the androgen sensitivity of the cancer cell has become lower, administering an effective amount of 1 or 2 compounds selected from an LHRH receptor agonist or antagonist and an antiandrogen drug, or a salt thereof, or when the androgen sensitivity of the cancer cell has increased, administering an effective amount of an androgen receptor agonist or a salt thereof, and 3) repeating the step 2) as necessary until disappearance or cure of the cancer, or reduction or maintenance of the volume of the cancer is achieved, wherein the LHRH receptor agonist is a peptide of the formula:

(Pyr)Glu-R$^1$-Trp-Ser-R$^2$-R$^3$-R$^4$-Arg-Pro-R$^5$     (I)

wherein R$^1$ is His, Tyr, Trp or p-NH$^2$-Phe; R$^2$ is Tyr or Phe; R$^3$ is Gly or a D type amino acid residue optionally having substituent(s); R$^4$ is Leu, Ile or Nle; and R$^5$ is Gly-NH—R$^6$, wherein R$^6$ is a hydrogen atom or an alkyl group optionally having a hydroxyl group, NH—R$^7$, wherein R$^7$ is a hydrogen atom, an amino group, an alkyl group optionally having a hydroxyl group, or —NH—CO—NH$_2$; wherein the D type amino acid residue for R$^3$ is a-D-amino acid having up to 9 carbon atoms, which is selected from the group consisting of D-Leu, Ile, Nle, Val, Nval, Abu, Phe, Phg, Ser, Thr, Met, Ala, Trp, and a-Aibu; the substituent for R$^3$ is selected from the group consisting of tert-butyl, tert-butoxy, tert-butoxycarbonyl, methyl, dimethyl, trimethyl, 2-naphthyl, indolyl-3-yl, 2-methylindolyl, and benzyl-imidazo-2-yl; and the alkyl group for R$^6$ or R$^7$ is a C$_{1-4}$ alkyl group selected from the group consisting of methyl, ethyl, propyl, isopropyl, butyl, isobutyl, sec-butyl and tert-butyl or a salt thereof;

the LHRH receptor antagonist is selected from the group consisting of abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione, 5-(N-benzyl-N-methylaminomethyl)-1-(2,6-difluorobenzyl)-6-[4-(3-ethylureido)phenyl]-3-phenylthieno [2,3-d]pyrimidine-2,4(1H,3H)-dione, and 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione hydrochloride; and the androgen receptor agonist is a steroidal androgen receptor agonist selected from the group consisting of dehydroepiandrosterone, testosterone, dihydrotestosterone, androstenedione, Mestanolone, Oxymesterone, Methandrostenolone, Fluoxymesterone, Chlorotestosterone acetate, Methenolone acetate, Oxymetholone, Stanozolol, Furazabol, Oxandrolone, 19-Nortestosterone, Norethandrolone, Ethylestrenol and Norbolethone, or a salt thereof.

3. The method of claim 2, which comprises alternately administering an effective amount of 1) an androgen receptor agonist or a salt thereof and 2) 1 or 2 compounds selected from an LHRH receptor agonist or antagonist and an antiandrogen drug, or a salt thereof.

4. The method of claim 3, comprising changing the administration drug after a lapse of 3 months to 5 years.

5. The method of claim 1, wherein the LHRH receptor agonist is selected from the group consisting of Leuprorelin, Gonadrelin, Buserelin, Triptorelin, Goserelin, Nafarelin, Histrelin, Deslorelin, Meterelin and Lecirelin.

6. The method of claim 2, wherein the LHRH receptor agonist is selected from the group consisting of Leuprorelin, Gonadrelin, Buserelin, Triptorelin, Goserelin, Nafarelin, Histrelin, Deslorelin, Meterelin and Lecirelin.

* * * * *